(12) United States Patent
Madabhushi et al.

(10) Patent No.: US 10,846,367 B2
(45) Date of Patent: Nov. 24, 2020

(54) PREDICTING RECURRENCE IN EARLY STAGE NON-SMALL CELL LUNG CANCER (NSCLC) WITH INTEGRATED RADIOMIC AND PATHOMIC FEATURES

(71) Applicant: Case Western Reserve University, Cleveland, OH (US)

(72) Inventors: Anant Madabhushi, Shaker Heights, OH (US); Xiangxue Wang, Cleveland Heights, OH (US); Pranjal Vaidya, Cleveland, OH (US); Vamsidhar Velcheti, Pepper Pike, OH (US)

(73) Assignee: Case Western Reserve University University, Cleveland, OH (US)

( * ) Notice: Subject to any disclaimer, the term of this patent is extended or adjusted under 35 U.S.C. 154(b) by 252 days.

(21) Appl. No.: 16/131,570

(22) Filed: Sep. 14, 2018

(65) Prior Publication Data
US 2019/0087532 A1    Mar. 21, 2019

Related U.S. Application Data

(60) Provisional application No. 62/558,979, filed on Sep. 15, 2017.

(51) Int. Cl.
*G06T 7/10* (2017.01)
*G06F 19/00* (2018.01)
(Continued)

(52) U.S. Cl.
CPC ......... *G06F 19/00* (2013.01); *G06K 9/00127* (2013.01); *G06K 9/3233* (2013.01); *G06K 9/4619* (2013.01); *G06K 9/4628* (2013.01); *G06K 9/6234* (2013.01); *G06K 9/6273* (2013.01); *G06K 9/6277* (2013.01); *G06K 9/6286* (2013.01); *G06K 9/66* (2013.01); *G06N 3/0454* (2013.01); *G06N 3/0472* (2013.01); *G06N 20/00* (2019.01); *G06T 7/0012* (2013.01); *G06T 7/0016* (2013.01); *G06T 7/10* (2017.01);
(Continued)

(58) Field of Classification Search
None
See application file for complete search history.

(56) References Cited

U.S. PATENT DOCUMENTS

2018/0142303 A1\*   5/2018   Showe ................ G16B 25/00
2018/0276498 A1\*   9/2018   Madabhushi ............ G06T 7/11
(Continued)

*Primary Examiner* — Fayyaz Alam
(74) *Attorney, Agent, or Firm* — Eschweiler & Potashnik, LLC

(57) ABSTRACT

Embodiments predict early stage NSCLC recurrence, and include processors configured to access a pathology image of a region of tissue demonstrating early stage NSCLC; extract a set of pathomic features from the pathology image; access a radiological image of the region of tissue; extract a set of radiomic features from the radiological image; generate a combined feature set that includes at least one member of the set of pathomic features, and at least one member of the set of radiomic features; compute a probability that the region of tissue will experience NSCLC recurrence based, at least in part, on the combined feature set; and classify the region of tissue as recurrent or non-recurrent based, at least in part, on the probability. Embodiments may display the classification, or generate a personalized treatment plan based on the classification.

22 Claims, 15 Drawing Sheets

(51) Int. Cl.
| | |
|---|---|
| *G06T 7/00* | (2017.01) |
| *G06K 9/66* | (2006.01) |
| *G06K 9/62* | (2006.01) |
| *G06K 9/32* | (2006.01) |
| *G06K 9/46* | (2006.01) |
| *G06N 3/04* | (2006.01) |
| *G06K 9/00* | (2006.01) |
| *G16H 20/10* | (2018.01) |
| *G16Z 99/00* | (2019.01) |
| *G16H 30/40* | (2018.01) |
| *G16H 40/63* | (2018.01) |
| *G16H 20/40* | (2018.01) |
| *G06N 20/00* | (2019.01) |
| *G16H 50/20* | (2018.01) |

(52) U.S. Cl.
CPC ............ *G16H 20/10* (2018.01); *G16H 20/40* (2018.01); *G16H 30/40* (2018.01); *G16H 40/63* (2018.01); *G16Z 99/00* (2019.02); *G06K 9/6218* (2013.01); *G06T 2207/10004* (2013.01); *G06T 2207/20036* (2013.01); *G06T 2207/20081* (2013.01); *G06T 2207/20084* (2013.01); *G06T 2207/30024* (2013.01); *G06T 2207/30061* (2013.01); *G06T 2207/30096* (2013.01); *G16H 50/20* (2018.01)

(56) References Cited

U.S. PATENT DOCUMENTS

2018/0333140 A1* 11/2018 Wodlinger ............ A61B 8/5246
2020/0167930 A1* 5/2020 Wang .................... G06T 7/0012

* cited by examiner

PREDICTING RECURRENCE IN EARLY STAGE NON-SMALL CELL LUNG CANCER (NSCLC) WITH INTEGRATED RADIOMIC AND PATHOMIC FEATURES

CROSS REFERENCE TO RELATED APPLICATIONS

This application claims the benefit of U.S. Provisional Application 62/558,979 filed Sep. 15, 2017, which is incorporated herein in its entirety.

FEDERAL FUNDING NOTICE

This invention was made with government support under grants 1U24CA199374-01, R01 CA202752-01 A1, R01 CA208236-01A1, R21 CA216579-01 A1, R21CA195152-01, R01DK098503-02, and 1 C06 RR012463-01 awarded by the National Institutes of Health. Also grants W81XWH-13-1-0418 and W81XWH-14-1-0323 awarded by the Department of Defense. The government has certain rights in the invention.

BACKGROUND

Non-small cell lung cancer (NSCLC) is the leading cause of cancer related deaths worldwide. NSCLC accounts for approximately 85% of all lung cancers. Early stage NSCLC accounts for approximately 40% of NSCLC patients, with 5-year survival rates varying between 31-49%. Early stage NSCLC refers to stage I or stage II NSCLC.

The treatment of choice for early stage NSCLC is complete surgical resection. Since there is a lack of a biomarker that can accurately stratify and predict disease risk in NSCLC patients, the decision to offer chemotherapy is primarily dependent on several clinical and visual radiographic biomarkers. Current treatment guidelines suggest adjuvant chemotherapy for patients with pathologic stage II disease, usually with resected tumor size greater than 4 cm. The incidence of local recurrence in early stage NSCLC varies from 6% to 55% with a median time of recurrence being fourteen months. Thus, a prognostic biomarker for early stage NSCLC would be advantageous in predicting recurrence and in planning adjuvant therapy.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
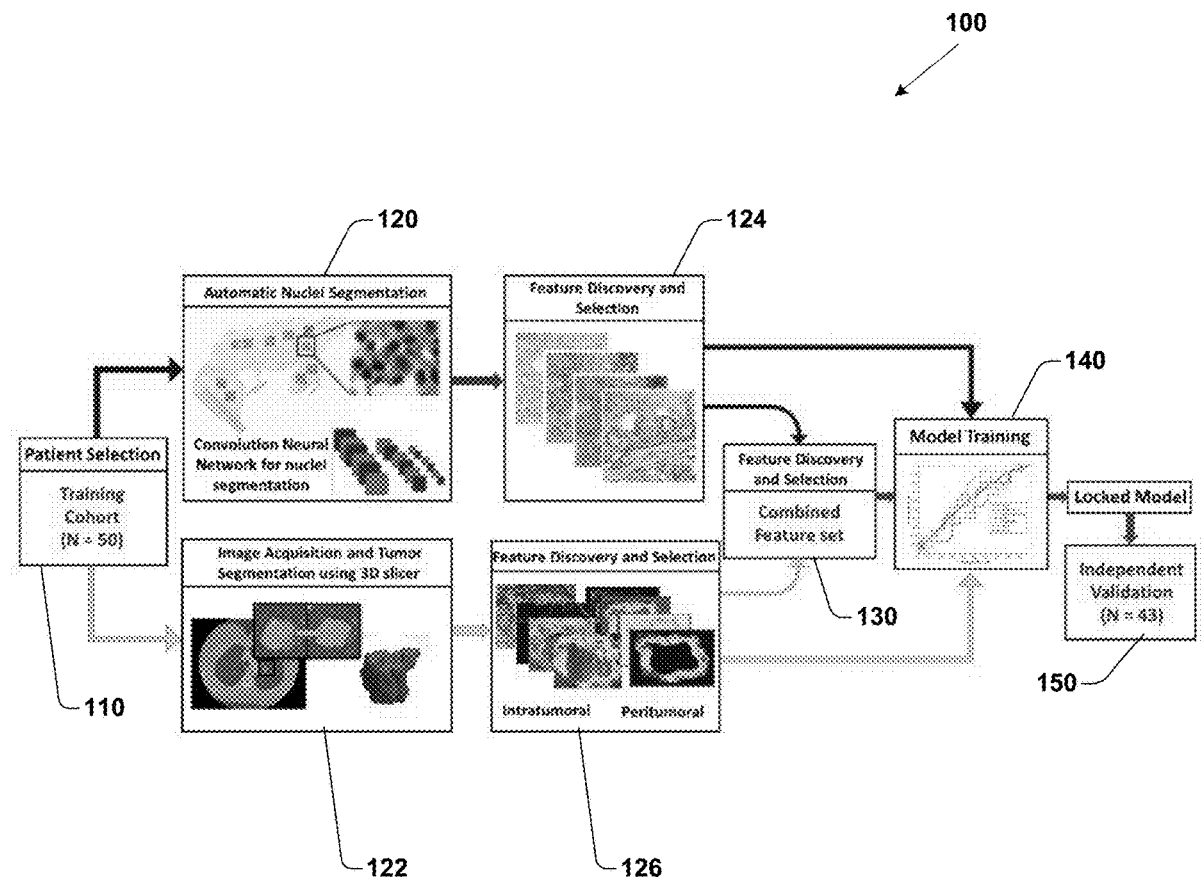
FIG. 1 is a workflow diagram of a method for training and validating a machine learning classifier for distinguishing early recurrence versus no/late recurrence in early stage NSCLC.

Lung cancer is the most significant cause of cancer related deaths among both men and women in the United States as well as worldwide. NSCLC accounts for approximately 85% of all lung cancers, and early stage NSCLC accounts for approximately 40% of all NSCLC patients. Five-year survival rates for NSCLC vary between 31% and 49%.

Complete surgical resection is the existing gold standard treatment for early stage NSCLC patients. Currently, the decision to offer chemotherapy is primarily dependent on clinical and visual radiographic factors, because there is a lack of a biomarker that can accurately stratify and predict disease risk in early stage NSCLC patients. There is not an established test or biomarker to aid an oncologist in identifying which early stage NSCLC patient will receive added benefit from adjuvant chemotherapy. Existing clinical and visual radiographic factors may be susceptible to inter-reviewer variability, or intra-reviewer variability, and are thus sub-optimal. Existing treatment guidelines for early stage NSCLC patients suggest the use of adjuvant chemotherapy only for pathologic stage II disease, usually with resected tumor size of greater than 4 cm. However, some patients with smaller sized tumors may also benefit from adjuvant therapy, but are not selected under existing guidelines, and thus fail to realize any benefit from adjuvant therapy. The incidence of local recurrence in early stage NSCLC varies from 6% to 55% with a median time of recurrence of fourteen months. Thus, a prognostic biomarker for early stage NSCLC would be advantageous for improved, more accurate prediction of recurrence, and for improved, more appropriately tailored adjuvant therapy planning.

Embodiments predict early stage NSCLC recurrence using a combined set of features that includes radiomic features extracted from computed tomography (CT) imagery, and pathomic features extracted from digitized imagery of tissue slides. Radiomics includes extracting high-throughput quantitative tumor imaging features from CT, positron emission tomography (PET), PET-CT, or magnetic resonance imaging (MRI) imagery. Radiomic textural features may be prognostic of disease recurrence and survival. Radiomic prognostic models may employ different feature selection techniques, different sampling techniques, including principle component analysis (PCA) feature selection, and synthetic minority over-sampling (SMOTE) sampling techniques.

The confirmation of the presence of NSCLC relies on histological examination of tumors in surgically resected specimens. Nuclear shape, nuclear architecture, and texture features, extracted from digitized whole slide images of tissue slides or tissue micro arrays (TMA) may be predictive of recurrence in early stage NSCLC. Shape and texture features may stratify risk of recurrence. Quantitative measurement of nuclear architecture and nuclear spatial arrangement may differ between low and high risk early stage NSCLC. Graphical representation of nuclear arrangement may also be employed to predict cancer grade, risk of progression, or biochemical recurrence.

Embodiments employ a combined set of radiomic features and pathomic features extracted at different imagery scales to predict recurrence in early stage NSCLC tumors. Embodiments integrate radiomic features extracted from pre-surgical CT imagery of a region of tissue at a first scale, with pathomic features extracted from tissue slide imagery of the region of tissue at a second, different scale, to create a unified predictor of recurrence in early stage NSCLC. Embodiments facilitate improved prediction of recurrence in early stage NSCLC compared to existing approaches, including approaches that may employ radiomic features or pathomic features independently. Embodiments facilitate the development of lower cost predictive companion diagnostic assays for identifying patients who may receive added benefit from adjuvant chemotherapy.

Example embodiments may include training a machine learning classifier to predict NSCLC recurrence using a training set of combined radiomic and pathomic features, and validating the performance of the machine learning classifier using a testing set of combined radiomic and pathomic features. In one embodiment, a training set of fifty early stage NSCLC cases was used to train a machine learning classifier. In this embodiment, an independent testing set of forty-three, different, early stage NSCLC cases was used to validate the performance of the machine learning classifier.

Embodiments employ digitized whole slide tissue specimens of a region of tissue demonstrating cancerous pathology for pathomic analysis, focusing specifically on tumor nuclei features. Nuclei represented in whole slide imagery are segmented using a deep learning approach. Histomorphometric features are extracted at a first scale from ten patches randomly selected from the digitized tissue slides.

To extract radiomic features from CT imagery of the region of tissue demonstrating cancerous pathology, a tumor region represented in the image is segmented. The tumor region may be segmented using automated segmentation approaches, or may be segmented manually. Radiomic features are extracted from the segmented tumor region, and also from a peritumoral region outside the segmented tumor region.

The radiomic features and pathomic features are combined to form a combined radiomic-pathomic feature set. In one embodiment, the combined radiomic-pathomic feature set is generated by selecting the top four most discriminative features from among the radiomic and pathomic features, where at least one feature is selected from each of the radiomic and pathomic feature sets. In one embodiment, an mRMR feature selection technique is employed.

FIG. 1 is a flowchart of an exemplary workflow of a method 100 for training and validating a machine learning classifier for distinguishing early versus no/late recurrence in early stage NSCLC, suitable for implementation by methods, operations, systems, apparatus, and other embodiments described herein. Method 100 includes, at 110, accessing a training cohort of patients demonstrating early stage NSCLC. In this embodiment, the training cohort includes fifty (50) patients. CT imagery and digitized whole slide imagery of a region of tissue demonstrating early stage NSCLC in the respective patients is accessed.

Method 100 also includes, at 120, segmenting cellular nuclei represented in the digitized whole slide imagery. In one embodiment, a convolutional neural network (CNN) may be used to automatically segment nuclei. Embodiments reduce the computational burden of examining all pixels at a higher magnification by selecting pixels which are likely to be nuclei to be examined at higher magnification using the CNN. Embodiments select pixels which are likely to be nuclei by first using the CNN to identify candidate nuclear pixels at the lower magnifications and then limiting the search space for the CNN at higher magnifications to locations previously identified at lower magnifications. Segmenting nuclei includes identifying the nucleus and corresponding nuclear boundary. In another embodiment, other automated techniques may be employed to segment nuclei. In one embodiment, the digitized whole slide imagery includes whole slide tissue images of early stage NSCLC patients with available pretreatment CT scans. The whole slide tissue images may be digitally scanned at 20× magnification, or other magnification level.

Method 100 also includes, at 124, generating a set of pathomic features by extracting pathomic features from the digitized whole slide imagery. The pathomic features are based on the segmented nuclei. The pathomic features are extracted from the digitized whole slide imagery at a first scale. The first scale may be, for example $10^{-7}$ m. Other scales may be employed. The scale may be a function of the magnification level. A tumoral region may be annotated within the pathomic image. The tumoral region may be annotated automatically using a machine learning annotation technique, or may be annotated manually by an expert human pathologist. Embodiments described herein divide the annotated pathomic image into a plurality of patches. In one embodiment, pathomic features are extracted from ten randomly selected patches from the tumoral region, a patch having dimensions of 1000 pixels by 1000 pixels. In another embodiment, other numbers of patches may be randomly selected. In another embodiment, a patch may have different dimensions (e.g., 750 pixels by 750 pixels, 2000 pixels by 2000 pixels).

In one embodiment, two hundred and forty-two nuclear (i.e., pathomic) features are extracted from the randomly selected patches, respectively, and averaged across the randomly selected patches. The pathomic features include global graph features, local nuclear cluster graph features, nuclear shape features, nuclear orientation entropy features, and nuclei texture features.

To extract global graph features, nuclear centroids are designated as graph nodes and the nodes are connected to build a variety of global nuclear graphs. The probability a first node will be connected with a second, different node is based on a pairwise Euclidean distance between the nodes. The probability may be weighted or tuned based on a characteristic of the image, or on a desired level of performance. From the global graphs, respectively, fifty-one (51) descriptors capturing the topology and spatial relation of nuclei are captured (i.e. Voronoi diagram). A graph is a mathematical construct comprising of a finite sets of objects (nodes) that capture global and local relationships via pairwise connections (edges) between the nodes. Graphs may be used to quantitatively characterize nuclear architecture in histopathologic images by representing the nuclei as nodes and subsequently quantifying neighborhood relationships (e.g., proximity) and spatial arrangement between the nodes.

Local nuclear cluster graphs first identify clusters of nuclei and then identify the centroid of the cluster. The cluster centroids are then used for defining nodes of the clusters. A similar set of topological and spatial relationship attributes are then mined from the local cluster graphs, respectively. Unlike the global graphs that reflect the micro-level, granular architecture of all individual nuclei, the local cluster graph is tuned to capture more macro-level, coarser measurement of nuclear arrangement. In one embodiment, twenty six (26) local nuclear cluster graph descriptors are extracted.

Nuclear shape features include a series of nuclear shape features that are extracted from the segmented boundary of members of the plurality of nuclei, respectively. Nuclear shape features may include a nuclear area feature, a perimeter feature, a min/max radius feature, or a Fourier transform of the nuclear contour feature. In one embodiment, one-hundred (100) nuclear shape descriptors are extracted.

Nuclear orientation entropy features facilitate predicting recurrence based on the property of recurrent disease that recurrent disease tissue will have higher nuclear orientation disorder and associated entropy compared to non-recurrent disease. The directionality of a member of the plurality of segmented nuclei is determined by performing principal component analysis on the Cartesian coordinate locations on the set of boundary points of members of the plurality of segmented nuclei, respectively. Second order statistics are calculated on the orientation of nuclei within local clusters. The second order statistics may include, for example, contrast energy, entropy, or other second order statistics. In one embodiment, a total of thirteen (13) second order nuclear orientation statistics are obtained for a nuclear cluster and the mean, median, and standard deviation measurements for these second order nuclear orientation statistics, respectively, are aggregated across ten regions of interest (ROI) across the whole slide images. In one embodiment, thirty nine (39) nuclear orientation entropy descriptors are extracted.

Nuclear texture features include gray level co-occurrence features that capture second order joint intensity statistics. Nuclear texture features encode the textural heterogeneity of the nucleus from which they are extracted. Embodiments compute thirteen second order texture features and for the thirteen second order texture features, respectively, the corresponding mean and standard deviation values are computed. In one embodiment, twenty six (26) nuclear texture descriptors are extracted.

Figure 3:
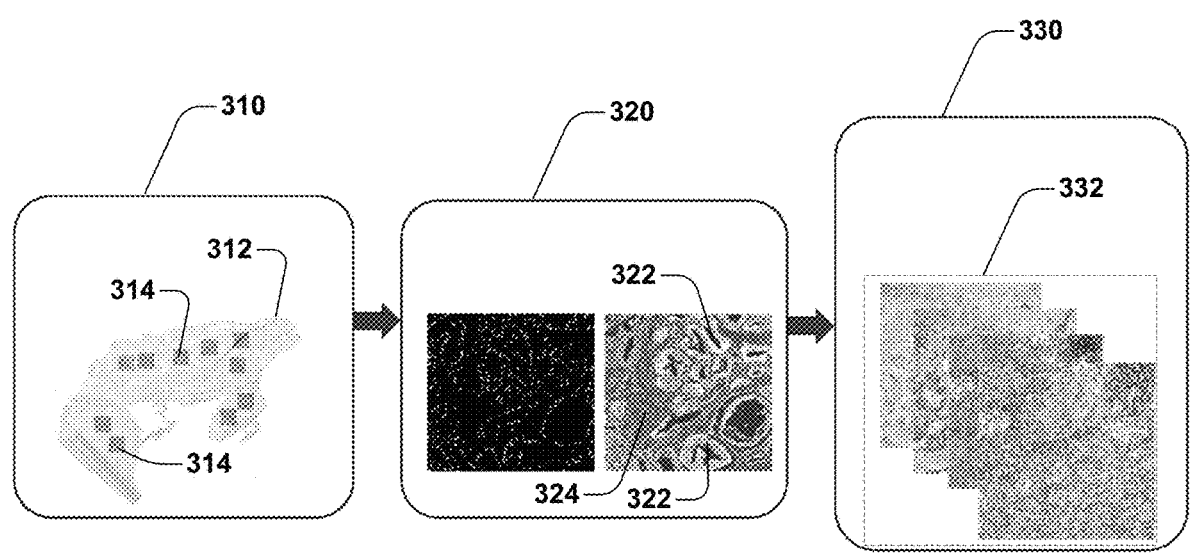
FIG. 3 is a workflow diagram of pathomic analysis.

FIG. 3 is a flowchart of an exemplary pathomic analysis workflow suitable for employment by embodiments described herein. FIG. 3 illustrates, at 310, a tile processing step. An annotated tumoral region 312 represented in a digitized whole slide image is divided into ten patches 314. In this example, the ten patches 314 have dimensions of 1000 pixels by 1000 pixels. A nuclei segmentation step is illustrated at 320, in which a convolutional neural network segments cellular nuclei 322 from other tissue 324 represented in the digitized whole slide image. A feature extraction step is illustrated at 330. Pathomic features 332 are extracted based, at least in part, on the segmented nuclei 322. While ten patches are illustrated, in another embodiment, another, different number of patches may be employed.

Figure 7:
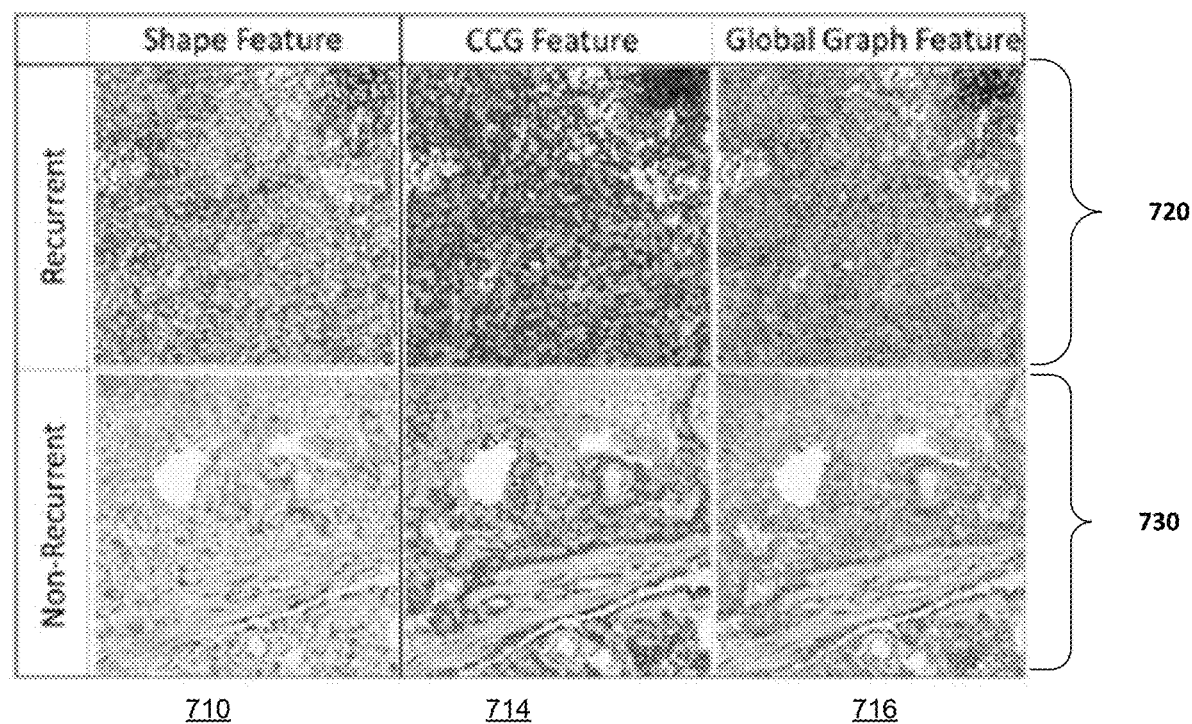
FIG. 7 illustrates representative pathomic features extracted from recurrent and non-recurrent NSCLC imagery.

FIG. 7 illustrates representative pathomic features of recurrent and non-recurrent NSCLC. A first row 720 includes pathomic features of recurrent NSCLC. A second row 730 includes pathomic features of non-recurrent NSCLC. Shape features are illustrated in column 710. Cluster graph features are illustrated in column 714. Global graph features are illustrated in column 716.

Method 100 also includes, at 122, segmenting a tumor region represented in the CT imagery. The tumor region may be segmented manually using a 3D slicer software, or may be segmented automatically. In one embodiment, the tumor region is segmented using a region growing technique, thresholding, or a watershed approach. The segmented tumor region includes a boundary that defines the tumor region, where the tumor region has a volume. The 3D tumor region is divided into a plurality of two dimensional (2D) sections. From the plurality of 2D sections that comprise the 3D volume of the tumor region, the 2D section with the largest area is selected for feature extraction. In another embodiment, different selection criteria may be used to select a 2D section from which to extract features. Method 100 also includes, at 126, extracting radiomic features from the CT imagery. The radiomic features are extracted at a second, different scale, compared to the first scale used in extracting pathomic features. For example, radiomic features may be extracted at a scale of $10^{-3}$ m. The radiomic features may be extracted from the segmented tumor region represented in the selected 2D section. Radiomic features may also be extracted from a peritumoral region represented in the selected 2D section. The peritumoral region is defined using a morphological transformation of the boundary, for example, dilation. In one embodiment, radiomic features are extracted from the peritumoral region in an annular ring fashion. For example, the boundary of the tumor region may be dilated incrementally, defining different annular rings. In one embodiment, five annular rings of 2 mm dilation are defined, out to a maximum radius of 10 mm from the tumor region boundary. The radiomic features may include Gabor features, Haralick features, Laws features, Law-Laplacian features, or co-occurrence of local anisotropic gradient orientation (CoLlAGe) features. Other radiomic features may also be extracted.

In one embodiment, forty-eight (48) Gabor descriptors are extracted. Gabor features use a Gabor wavelet filter to detect edges using specific frequencies and orientations. For example, embodiments may employ frequencies of ($f \in [0, 2, 4, 8, 16, 32]$) and orientations of ($\theta \in \{0, \pi/8, \pi/4, 3\pi/8, \pi/2, 5\pi/8, 3\pi/8, \pi/2, 5\pi/8, 3\pi/4, 7\pi/8\}$). In another embodiment, another, different number of Gabor descriptors may be extracted.

In one embodiment, thirteen (13) Haralick descriptors are extracted. Haralick features quantify heterogeneity and entropy of local intensity textures using a gray-level co-occurrence matrix. In another embodiment, another, different number of Haralick descriptors may be extracted.

In one embodiment, twenty-five (25) Laws descriptors are extracted. Laws features represent responses to a square window filter targeting combinations of specific textural enhancement patterns in the X and Y directions. Embodiments extract combinations of five one-dimensional (1D) filters, including level (L), edge (E), spot (S), wave (W), and ripple (R). In another embodiment, another, different number of Laws descriptors may be extracted.

In one embodiment, thirteen (13) CoLIAGe descriptors are extracted. CoLIAGe descriptors apply Haralick metrics to intensity gradient orientations within a predefined square window. CoLIAGe features capture subtle differences between benign and pathologic phenotypes which are visually indistinguishable on routine anatomic imaging. Dominant gradient orientation along the X and Y direction is computed for pixels in the window, respectively, via principle component analysis. A corresponding co-occurrence matrix is computed for pixels in the window, respectively, to capture the dominant orientation. In one embodiment, the corresponding co-occurrence matrix is computed for each pixel in the window. In another embodiment, the corresponding co-occurrence matrix is computed for a threshold number of pixels (i.e., 75%, 90%) in the window. In embodiments described herein, a 5 by 5 pixel window is employed when radiomic features are extracted at a scale of $10^{-3}$ m. In another embodiment, other window sizes may be employed.

Figure 2:
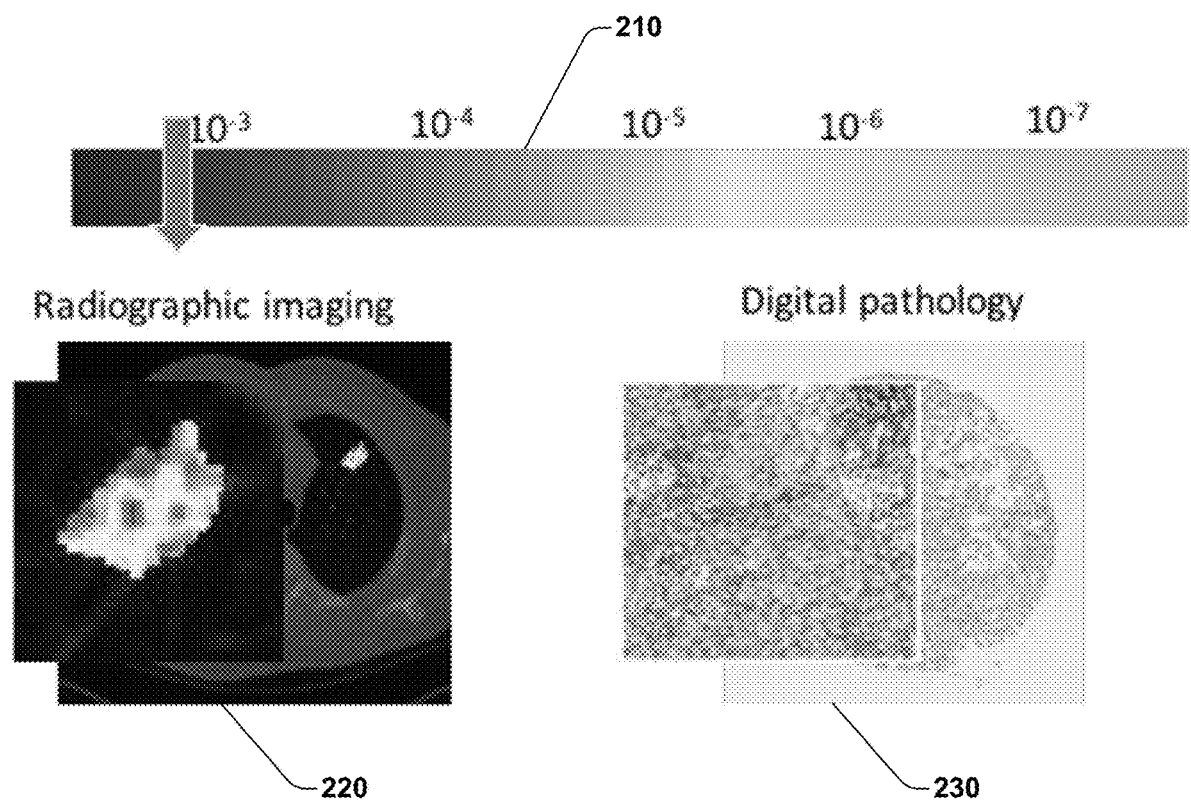
FIG. 2 illustrates a diversity of scale lengths for different imaging modalities.

FIG. 2 illustrates an example of a diversity of scale lengths for different imaging modalities. A legend 210 indicates a range of image scales, from $10^{-3}$ m to $10^{-7}$ m. A heatmap 220 of a radiomic feature extracted from CT imagery of a tumor region segmented from a region of tissue demonstrating NSCLC is illustrated. The radiomic feature is extracted from the CT imagery at a scale of, in this example, $10^{-3}$ m. A digital pathology slide 230 of the region of tissue is also illustrated. Pathomic features are extracted at a scale of $10^{-7}$ m in this example.

Figure 4:
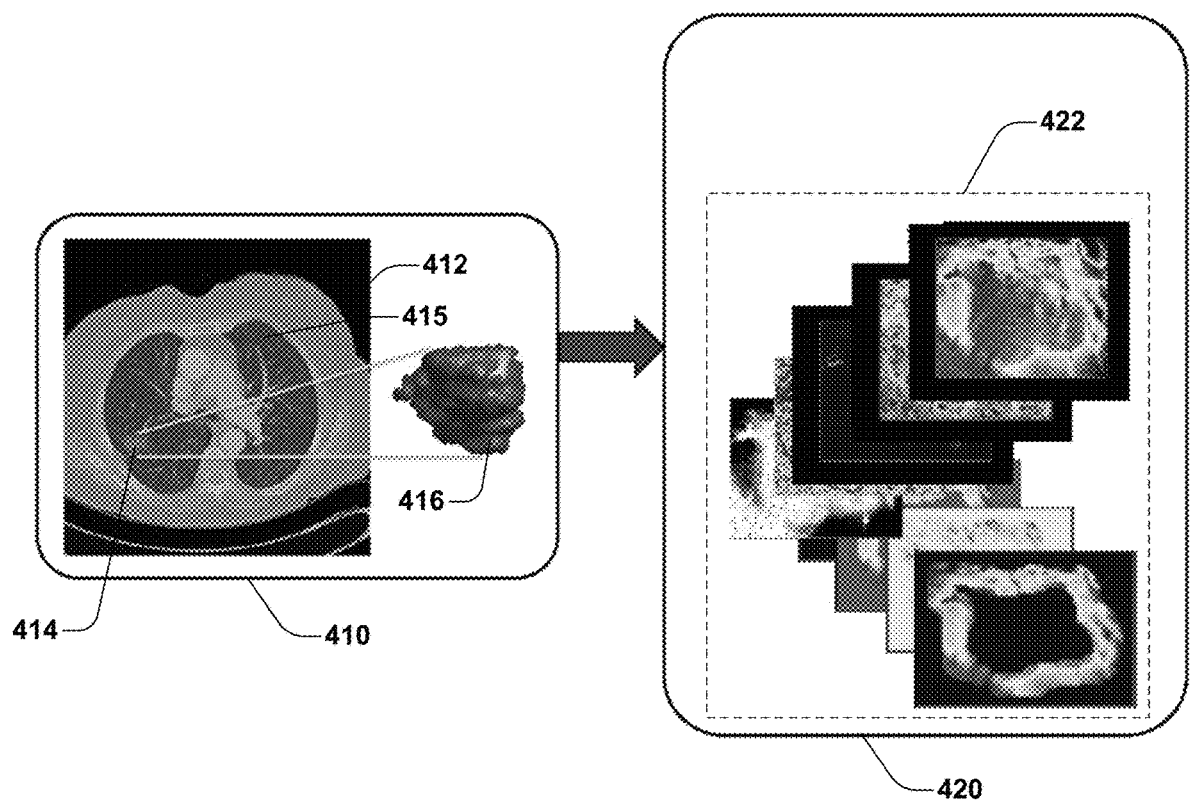
FIG. 4 is a workflow diagram of radiomic analysis.

FIG. 4 is a flowchart of an exemplary radiomic analysis workflow suitable for employment by embodiments described herein. A segmentation step is illustrated at 410. A CT image 412 of a region of tissue demonstrating early stage NSCLC includes a tumoral region 414 segmented from non-tumoral region 415. A magnified representation 416 of the 3D tumoral region is illustrated. A feature extraction step is illustrated at 420. Radiomic features 422 are extracted from the tumoral region 414 and peritumoral region as described herein, and may include, for example, Gabor features, Laws features, Laplace features, Haralick features, or CoLIAGe features.

Figure 6:
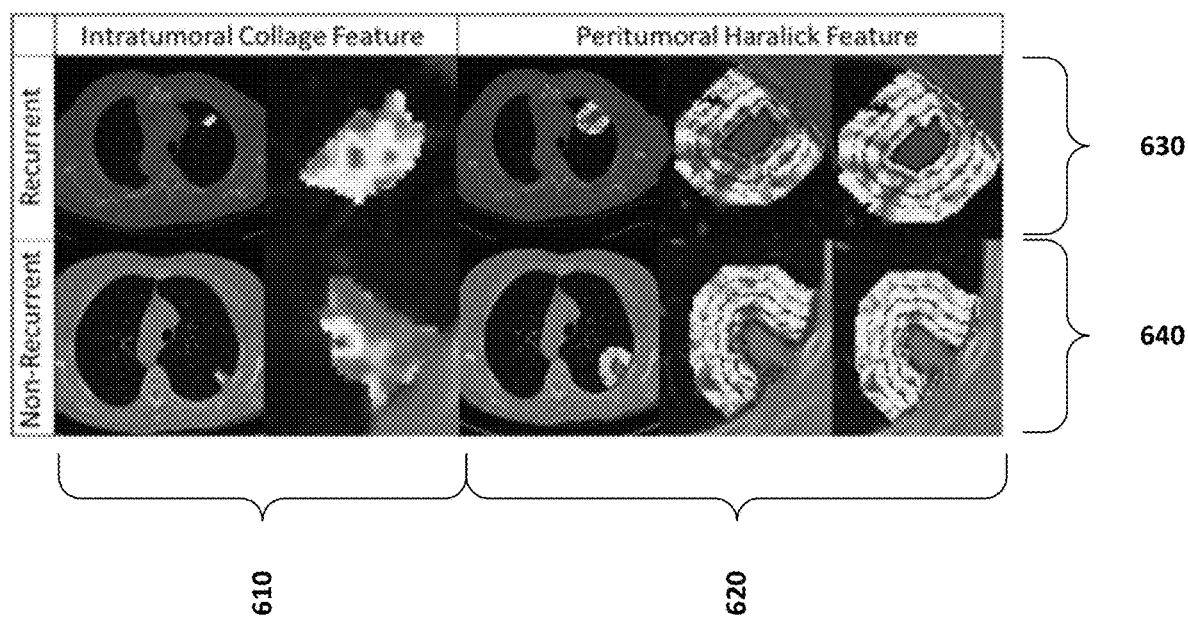
FIG. 6 illustrates representative radiomic features extracted from recurrent and non-recurrent early stage NSCLC imagery.

FIG. 6 illustrates representative radiomic features used by embodiments for predicting recurrent and non-recurrent early stage NSCLC. Intratumoral CoLIAGe features are illustrated in column 610. Peritumoral Haralick features are illustrated in column 620. Radiomic features for predicting recurrent NSCLC are illustrated in the top row 630. Radiomic features for non-recurrent NSCLC are illustrated in the bottom row 640.

Method 100 also includes, at 130, generating a combined feature set. The combined feature set includes features selected from the pathomic features set and from the radiomic features set. The combined feature set may include at least four features, including at least one feature selected from the radiomic features, and at least one feature selected from the pathomic features. The combined feature set includes the most discriminating features with respect to predicting recurrence and non-recurrence, as determined using, for example, minimum redundancy, maximum relevance (mRMR) feature selection, or other feature selection techniques. mRMR feature selection identifies a combination of features that together maximize the joint dependency for distinguishing binary classes (e.g., recurrence vs. non-recurrence) while minimizing the redundancy within the feature combination. To reduce the risk of overfitting, embodiments may select the top four features from the radiomic features and the pathomic features from a training cohort of images using a three-fold cross validation framework over two-hundred (200) iterations. In another embodiment, other feature selection techniques, validation frameworks, or number of iterations may be employed.

Method 100 also includes, at 140, training a machine learning classifier using the combined feature set. Training the machine learning classifier may include training different types of machine learning classifiers using the combined feature set. For example, in one embodiment, the identical subset of features (e.g., the combined feature set) is fed to construct a linear discriminant analysis (LDA) classifier, a quadratic discriminant analysis (QDA) classifier, and a support vector machine (SVM) classifier. In one embodiment, a training set of fifty (50) training cases was employed to train and lock down the machine learning classifier using the combined feature set. The training set includes CT imagery, and digitized images of hematoxylin and eosin (H&E) stained whole slide images.

Method 100 also includes, at 150, validating the machine learning classifier. In one embodiment, a testing set of imagery acquired from forty-three (43) NSCLC patients independent of the training set is employed. In this embodiment, thirty (30) of the training set patients demonstrated squamous cell (SC) cancer, and thirteen (13) remaining patients demonstrated adenocarcinoma. In one embodiment, the testing set is acquired from a publically accessible cancer genome atlas (e.g., TCGA) as an independent validation set.

In one embodiment, inclusion criteria for both the training set and the testing set includes only early stage (e.g., stage I, stage II) cancer and those patients who have clinical information on recurrence and survival time available, and who have tissue slides available. Patients with later stage cancer, lack of recurrence information, and who lack co-existing tissue slides are excluded. CT imagery includes baseline helical CT imagery.

In one embodiment, a supervised approach is employed to evaluate the top most discriminative features on the different machine learning classifiers. Area under the receiver operating curve (AUC) is calculated for the different classifiers respectively, for distinguishing early versus non/late recurrence on the training cohort, as well as the testing cohorts. The top most discriminative or predictive features may be identified using box and whisker plots and feature maps, or other statistical techniques. Additionally, Kaplan Meier survival analysis curves may be employed to correlate recurrence free survival (RFS) with each classifier model. RFS is measured from the date of surgery to the date of death or the date of recurrence, whichever occurs first. Patients who leave the study or die prior to a five year threshold are excluded from the training set and the testing set.

Figure 5:
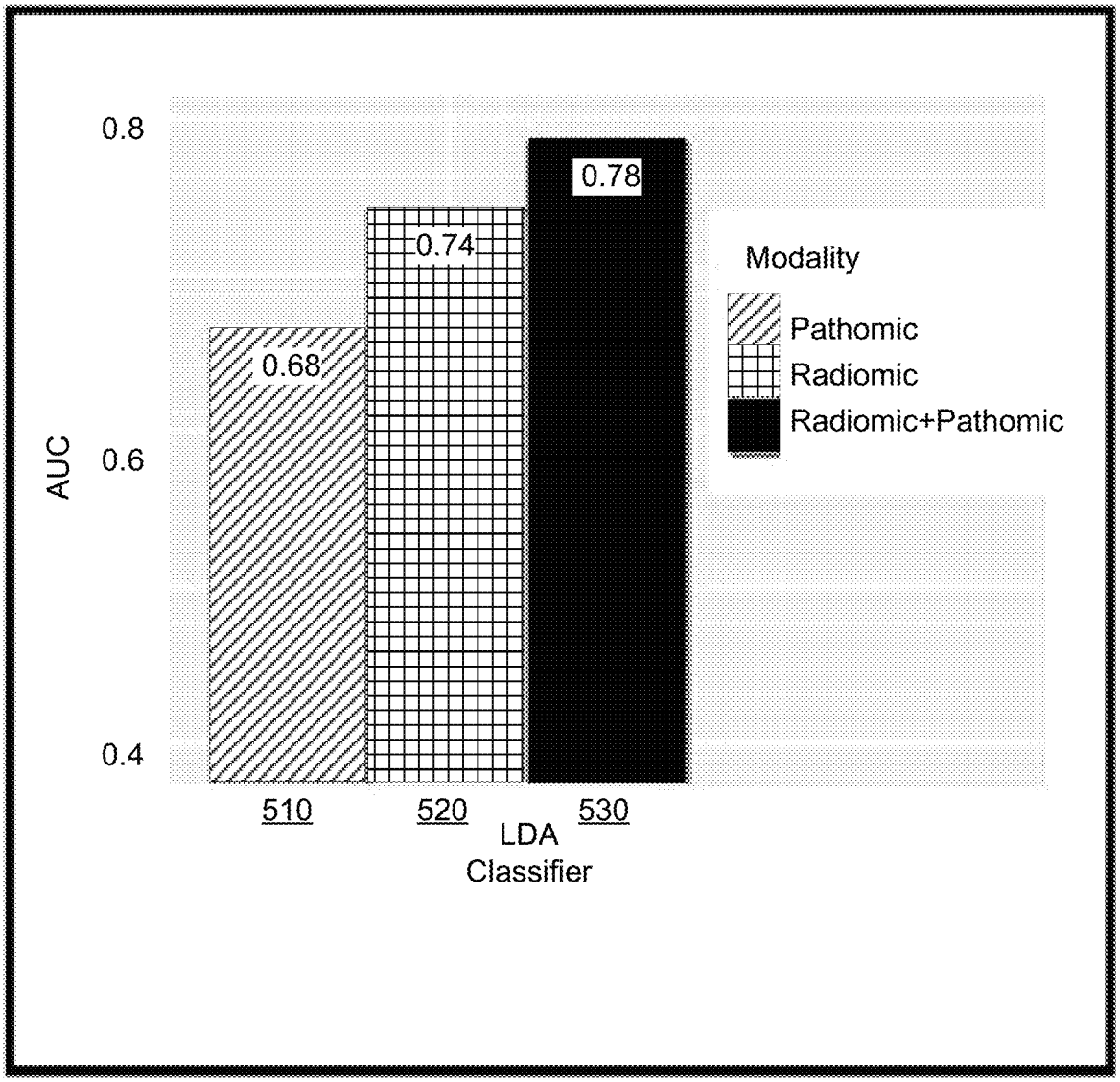
FIG. 5 is a bar chart comparing classifier performance.

Embodiments measurably improve on existing approaches to predicting recurrence in early stage NSCLC. FIG. 5 illustrates a bar chart 500 of AUC values for LDA classifiers that employ only radiomic features, only pathomic features, or a combined radiomic pathomic feature set. The y-axis indicates AUC values. The x-axis indicates LDA classifiers using only pathomic features 510, only radiomic features 520, and combined radiomic and pathomic features 530. Embodiments that employ an LDA classifier using combined radiomic and pathomic features achieve and AUC of at least 0.78, compared to 0.74 and 0.68 for just radiomic or pathomic features, respectively. Embodiments thus offer a measurable improvement in the prediction of NSCLC recurrence of over 4% and 10% over existing approaches. By improving the accuracy with which NSCLC recurrence is predicted, embodiments improve the performance of the machine on which embodiments are implemented.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 8:
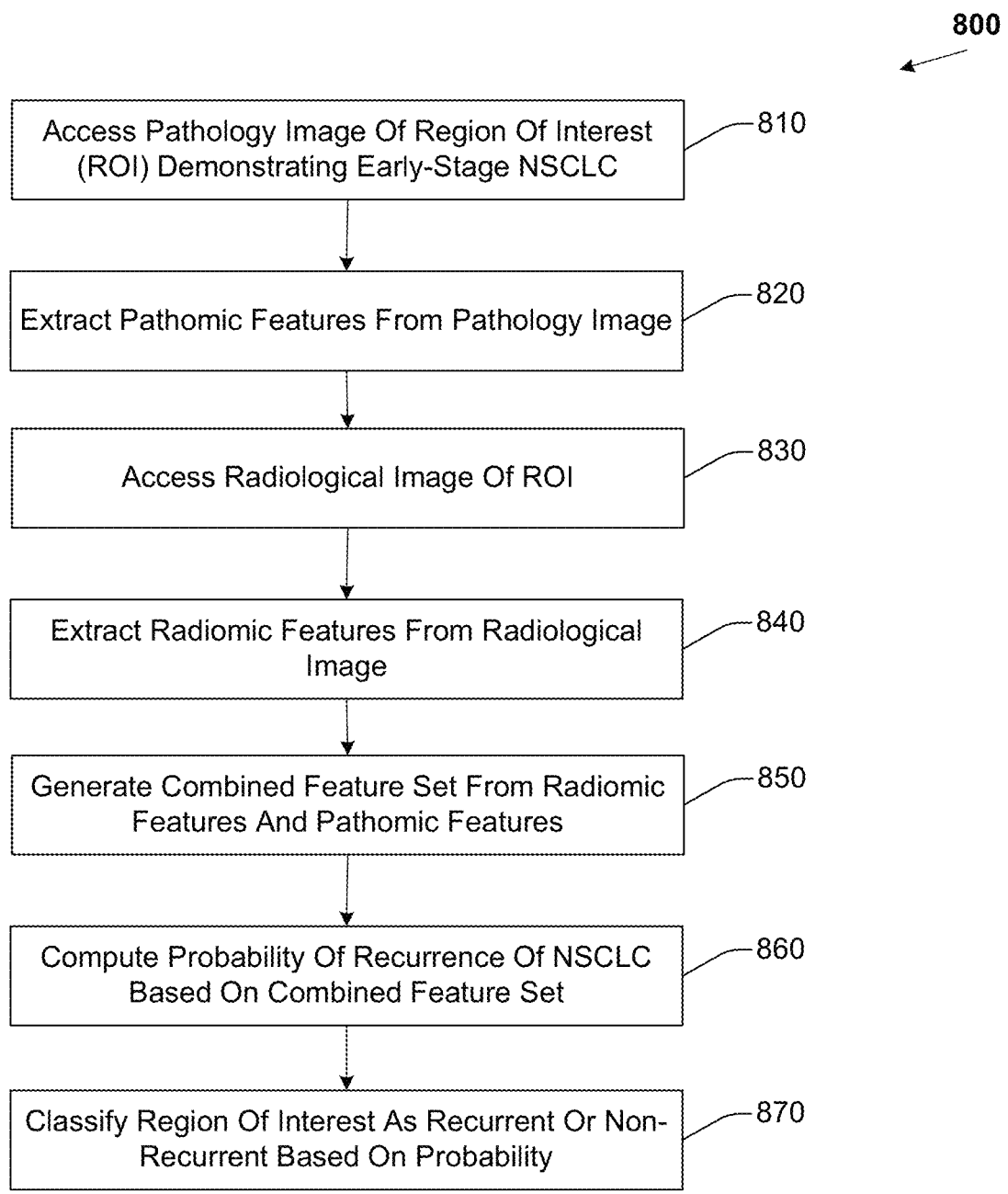
FIG. 8 is a flow diagram of example operations for predicting recurrence of early stage NSCLC.

FIG. 8 is a flow diagram of example operations 800 that may be performed by a processor for predicting early stage NSCLC recurrence. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 800 includes, at 810, accessing a pathology image of a region of tissue demonstrating early stage NSCLC. The pathology image includes an NSCLC tumor region. The pathology image includes a representation of a plurality of cellular nuclei. Accessing the pathology image includes acquiring electronic data, reading from a computer file, receiving a computer file, reading from a computer memory, or other computerized activity. The pathology image has a plurality of pixels, a pixel having an intensity. In one embodiment, the pathology image is a digitized H&E stained image scanned at 20× magnification. In another embodiment, the image may be acquired using other, different imaging parameters, including different sizes, staining techniques, or scanning magnification levels.

The set of operations 800 also includes, at 820, extracting a set of pathomic features from the pathology image. In one embodiment, extracting the set of pathomic features includes segmenting at least two members of the plurality of cellular nuclei represented in the pathology image. In one embodiment, a convolutional neural network (CNN) is employed to segment the at least two members of the plurality of cellular nuclei. In another embodiment, the pathology image includes a pre-segmented plurality of cellular nuclei. Extracting the set of pathomic features further includes extracting the set of pathomic features based on the at least two segmented members of the plurality of cellular nuclei. In one embodiment, the set of pathomic features includes at least one of a global graph feature, a local nuclear cluster graph feature, a nuclear shape feature, or a nuclear orientation entropy feature.

In one embodiment, the pathology image includes a first plurality of patches. A member of the first plurality of patches has dimensions smaller than the size of the pathology image. For example, in one embodiment, a member of the first plurality of patches has dimensions of one-thousand (1000) pixels by one-thousand (1000) pixels, where the pathology image has larger dimensions (e.g., 20,000 pixels by 20,000 pixels). In this embodiment, the set of pathomic features is extracted from a second plurality of patches selected randomly from the first plurality of patches. For example, in this embodiment, the set of pathomic features is extracted from ten members of the first plurality of patches. In another embodiment, the set of pathomic features may be extracted from a different number of randomly selected patches (e.g., 8 patches, 12 patches), or from patches with different dimensions (e.g., 500 pixels by 500 pixels). In one embodiment, patches are accepted randomly and in a non-overlapping fashion. Embodiments select the number of patches to appropriately sample multiple different regions within the landscape of the tissue image, typically there being more patches within larger whole slide images compared to smaller sized images.

The set of operations 800 also includes, at 830, accessing a radiological image of the region of tissue. Accessing the radiological image includes acquiring electronic data, reading from a computer file, receiving a computer file, reading from a computer memory, or other computerized activity. In one embodiment, the radiological image is a 3D CT image that includes a representation of a tumor region. The radiological image includes a plurality of pixels, a pixel having an intensity.

The set of operations 800 also includes, at 840, extracting a set of radiomic features from the radiological image. In one embodiment, extracting the set of radiomic features from the radiological image includes extracting tumoral radiomic features, and extracting peritumoral radiomic features from the radiological image. The set of radiomic features, including tumoral radiomic features and peritumoral radiomic features, includes at least one of a Gabor feature, a Haralick feature, a Laws feature, a Law-Laplacian feature, or a CoLIAGe feature. In one embodiment, the set of radiomic features are extracted from a 5 mm by 5 mm window of the radiological image. In another embodiment, other, different window sizes may be used.

Figure 9:
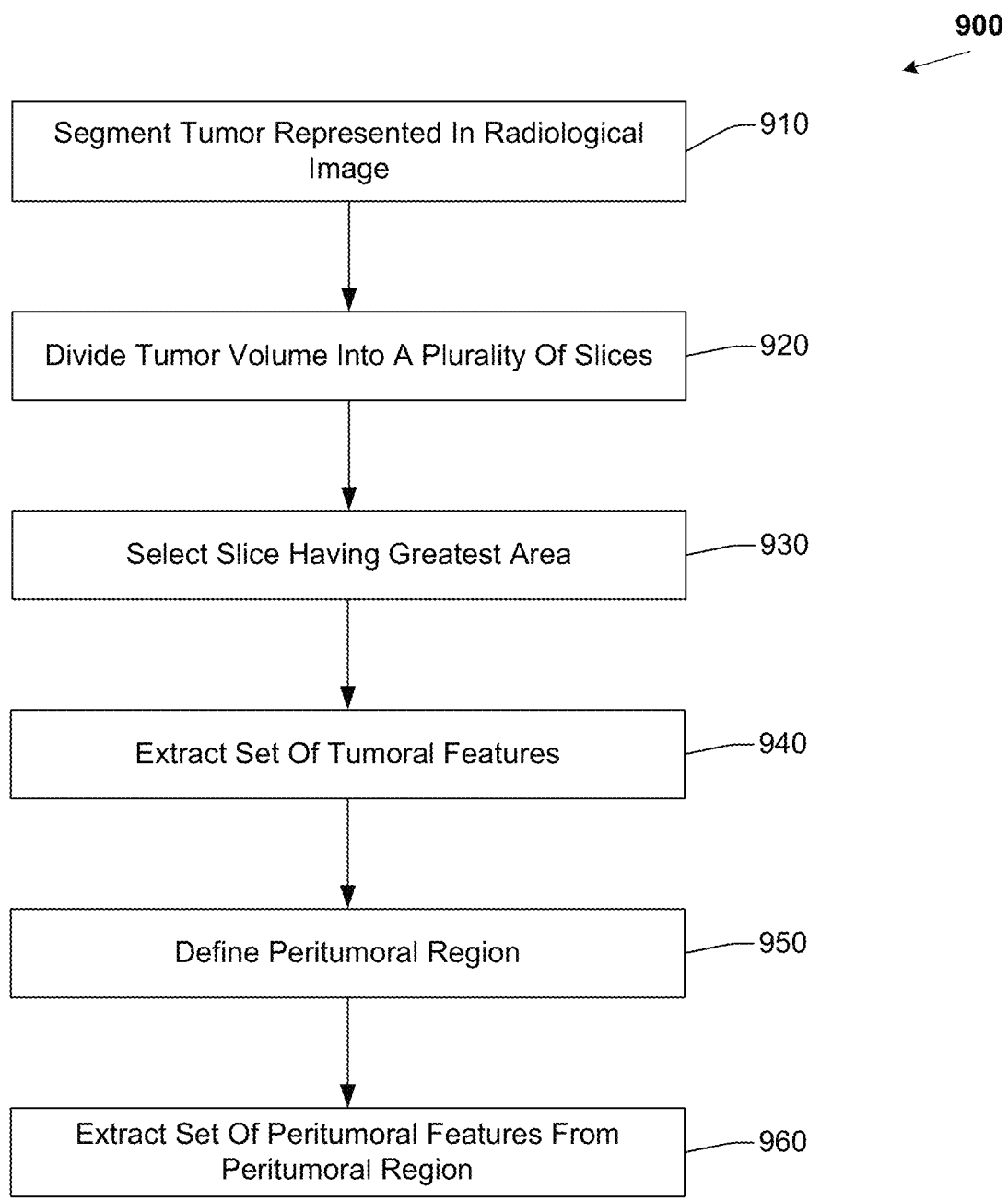
FIG. 9 is a flow diagram of example operations for extracting radiomic features from a radiological image.

FIG. 9 illustrates a set of operations 900 for extracting the set of radiomic features from the radiological image suitable for use by embodiments described herein, including operations 800 and 1500 The set of operations 900 includes, at 910 segmenting a tumor represented in the radiological image, where the tumor has a volume. In one embodiment, the tumor is segmented using a watershed technique. In another embodiment, other segmentation techniques may be employed.

The set of operations 900 also includes, at 920, dividing the volume into a plurality of slices. A slice has a boundary. A slice also has an area defined by the boundary. The number of slices in the plurality may be a function of the volume, may be a function of a desired level of computational complexity, or may be user defined.

The set of operations 900 also includes, at 930, selecting a member of the plurality of slices having the largest area. In a situation in which two different slices have the same area, a slice may be selected randomly, may be selected manually, or may be selected base on other criteria, including nearness to the centroid of the tumor.

The set of operations 900 also includes, at 940, extracting a set of tumoral features from the member of the plurality of slices. The set of tumoral features includes at least one of a Gabor feature, a Haralick feature, a Laws feature, a Law-Laplacian feature, or a CoLIAGe feature.

Figure 10:
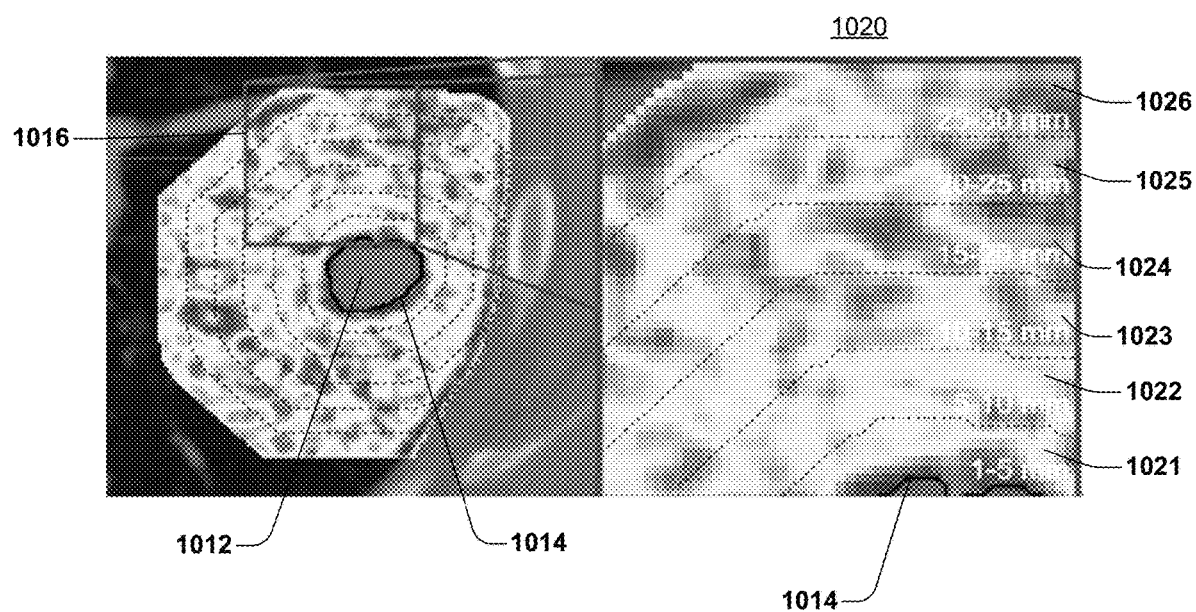
FIG. 10 illustrates annular rings of a peritumoral region.

The set of operations 900 also includes, at 950, defining a peritumoral region based on the boundary of the member of the plurality of slices. The peritumoral region may include a plurality of annular rings. An annular ring is defined by embodiments by applying a morphological operation to the boundary. For example, the boundary may be dilated a first incremental amount to generate a first annular ring. In one embodiment, the peritumoral region includes five annular rings, generated with a dilation increment of 2 mm. Thus, a first annular ring would include a region extending from the boundary outward 2 mm, a second annular ring would include a region extending from the 2 mm dilation to 4 mm, and so on. FIG. 10 illustrates annular rings 1021-1026 of a peritumoral region 1016. FIG. 10 illustrates a slice of a tumor volume represented in CT imagery. A tumor region 1012 includes a boundary 1014. A peritumoral region 1016 including six annular rings is defined by dilating the boundary 1014. The six annular rings 1021-1026 are illustrated at a greater magnification at 1020. In this example, the annular rings are dilated from the boundary 1014 at a dilation increment of 5 mm, although in other embodiments, other dilation increments may be employed. In another embodiment, the peritumoral region may be defined using other techniques. For example, a set of concentric spheres may be defined around the centroid of the tumor.

The set of operations 900 further includes, at 960, extracting a set of peritumoral features from the peritumoral region. The set of peritumoral features includes at least one of a Gabor feature, a Haralick feature, a Laws feature, a Law-Laplacian feature, or a CoLIAGe feature.

Returning to the set of operations 800, the set of operations 800 also includes, at 850, generating a combined feature set. The combined feature set includes at least one member of the set of pathomic features, and at least one member of the set of radiomic features. Generating the combined feature set includes selecting the top most discriminative features from among the pathomic features and the radiomic features. In one embodiment, the combined feature set includes features selected using 3-fold cross validation using mRMR feature selection. In another embodiment, other feature selection techniques may be employed. Selecting at least one feature from the radiomic feature set, and at least one feature from the pathomic feature set, ensures that neither set is over-represented.

The set of operations 800 also includes, at 860, computing a probability that the region of tissue will experience NSCLC recurrence. The probability is computed based, at least in part, on the combined feature set. In one embodiment, computing the probability that the region of tissue will experience recurrence includes providing the combined feature set to a machine learning classifier. In one embodiment, the machine learning classifier is an LDA classifier configured to discriminate early stage NSCLC tissue that experiences recurrence from early stage NSCLC tissue that does not experience recurrence. The machine learning classifier computes the probability based, at least in part, on the combined feature set. In this embodiment, computing the probability further includes receiving from the machine learning classifier, the probability.

The set of operations 800 also includes, at 870, classifying the region of tissue as recurrent or non-recurrent. The classification is based, at least in part, on the probability. The region of tissue may also be classed as, for example, "likely to experience recurrence", "unlikely to experience recurrence", or other classification based on the probability.

In one embodiment, the set of operations 800 further includes displaying the classification. In another embodiment, the set of operations 800 also includes displaying at least one of the probability, the pathology image, the radiological image, the set of pathomic features, the set of radiomic features, or the combined set of features. Displaying the classification and at least one of the probability, the pathology image, the radiological image, the set of pathomic features, the set of radiomic features, or the combined set of features may include displaying the classification and at least one of the probability, the pathology image, the radiological image, the set of pathomic features, the set of radiomic features, or the combined set of features on a computer monitor, a smartphone display, a tablet display, or other displays. Displaying the classification and at least one of the probability, the pathology image, the radiological image, the set of pathomic features, the set of radiomic features, or the combined set of features may also include printing the classification and at least one of the probability, the pathology image, the radiological image, the set of pathomic features, the set of radiomic features, or the combined set of features. Displaying the classification and at least one of the probability, the pathology image, the radiological image, the set of pathomic features, the set of radiomic features, or the combined set of features may also include controlling a computer assisted diagnosis (CADx) system, a monitor, or other display, to display operating parameters or characteristics of the machine learning classifier, during both training and testing, or during clinical operation of the machine learning classifier. By displaying the classification and at least one of the probability, the pathology image, the radiological image, the set of pathomic features, the set of radiomic features, or the combined set of features, example embodiments provide a timely and intuitive way for a human pathologist to more accurately classify pathologies demonstrated by a patient, thus improving on existing approaches to predicting disease recurrence.

In one embodiment, the set of operations 800 further includes controlling a processor or a personalized NSCLC treatment plan system to generate a personalized treatment plan. The personalized treatment plan is based, at least in part, on the classification. In one embodiment, the personalized treatment plan is further based on at least one of the combined set of features, the radiological image, or the pathology image. Generating a personalized treatment plan facilitates delivering a particular treatment that will be therapeutically active to the patient, while minimizing negative or adverse effects experienced by the patient. For example, the personalized treatment plan may suggest a surgical treatment, may define an immunotherapy agent dosage or schedule, or a chemotherapy agent dosage or schedule, when the region of tissue is classified as likely to experience recurrence. For a region of tissue classified as unlikely to experience recurrence, other treatments may be suggested.

In one embodiment, the operations 800 further include training the machine learning classifier. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which pathomic features and which radiomic features are most discriminative in distinguishing tissue likely to experience recurrence from tissue unlikely to experience recurrence.

While FIG. 8 illustrates various actions occurring in serial, it is to be appreciated that various actions illustrated in FIG. 8 could occur substantially in parallel. By way of illustration, a first process could involve accessing a pathology image, a second process could involve accessing a radiological image, and a third process could involve extracting pathomic features from the pathology image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods 100 or 1400, operations 800, 900, or 1500, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved classification of tissue demonstrating early stage NSCLC may produce the technical effect of improving treatment efficacy by increasing the accuracy of and decreasing the time required to treat patients demonstrating early stage NSCLC, or other forms of cancerous pathology. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted. Controlling a personalized medicine system, a CADx system, a processor, or NSCLC recurrence prediction system based on improved, more accurate identification or classification of tissue further improves the operation of the system, processor, or apparatus, since the accuracy of the system, processor, or apparatus is increased and unnecessary operations will not be performed. Embodiments described herein, including at least methods 100 or 1400, the sets of operations 800, 900, and 1500, apparatus 1100 and 1200 resolve features extracted from digitized H&E stained images and CT imagery at a higher order or higher level than a human can resolve in the human mind or with pencil and paper. For example, the local cluster graphs are not biological properties of cancerous tissue that a human eye can perceive. A tumor does not include a set of pixels with intensities, a set of cluster graphs or entropy features, and these features cannot be stored in a human mind. Embodiments described herein use a combined order of specific rules, elements, operations, or components that render information into a specific format that is then used and applied to create desired results more accurately, more consistently, and with greater reliability than existing approaches, thereby improving the performance of the machine, computer, or system with which embodiments are implemented.

Using a more appropriately modulated treatment may lead to less aggressive therapeutics being required for a patient or may lead to avoiding or delaying a biopsy, a resection, or other invasive procedure. When patients demonstrating early stage NSCLC who are likely to experience recurrence are more accurately distinguished from patients who are unlikely to experience recurrence, patients most at risk may receive a higher proportion of scarce resources (e.g., therapeutics, physician time and attention, hospital beds) while those less likely to benefit from the treatment, or less in need, may be spared unnecessary treatment, which in turn spares unnecessary expenditures and resource consumption. Example methods, apparatus, and other embodiments may thus have the additional effect of improving patient outcomes and reducing patient suffering compared to existing approaches.

Figure 11:
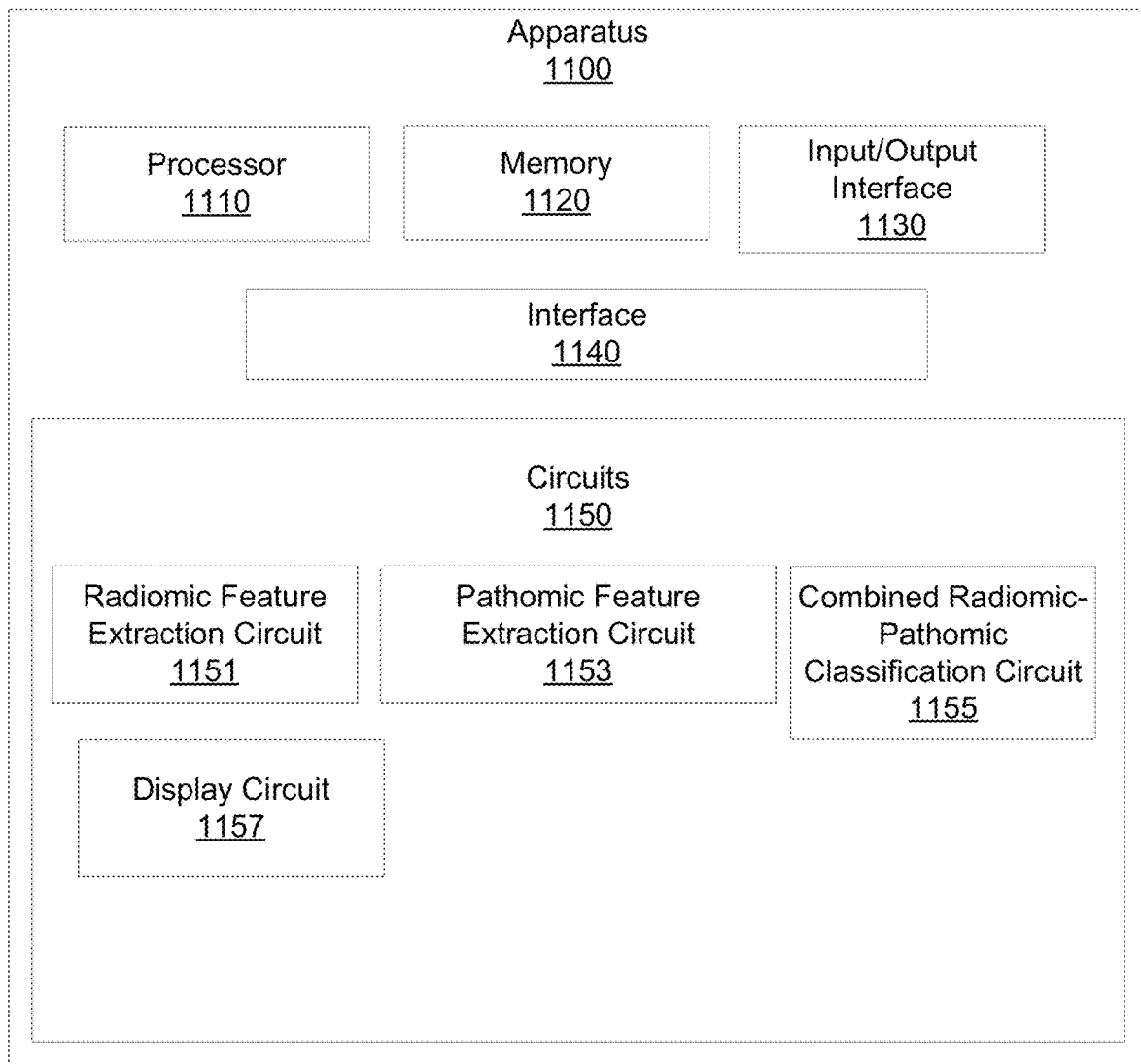
FIG. 11 illustrates an example apparatus for predicting recurrence of early stage NSCLC.

FIG. 11 illustrates an example apparatus 1100 for predicting recurrence of early stage NSCLC. Apparatus 1100 includes a processor 1110. Apparatus 1100 also includes a memory 1120. Processor 1110 may, in one embodiment, include circuitry such as, but not limited to, one or more single-core or multi-core processors. Processor 1110 may include any combination of general-purpose processors and dedicated processors (e.g., graphics processors, application processors, etc.). The processors may be coupled with or may include memory (e.g. memory 1120) or storage and may be configured to execute instructions stored in the memory or storage to enable various apparatus, applications, or operating systems to perform the operations. Memory 1120 is configured to store a digitized pathology image of a tissue slide of a region of tissue demonstrating early stage NSCLC. Memory 1120 is further configured to store a radiological image of the region of tissue. The digitized pathology image has a plurality of pixels, a pixel having an intensity. The radiological image has a plurality of pixels, a pixel having an intensity. In one embodiment, the digitized pathology image is a digitized H&E stained image scanned at 20× magnification. In another embodiment, the image may be acquired using other, different imaging parameters, including different sizes, staining techniques, or scanning magnification levels. In one embodiment, the radiological image is a 3D CT image that includes a representation of a tumor region represented in the digitized pathology image. Memory 1120 may be further configured to store a training set that includes a plurality of digitized images of H&E stained slides of a region of tissue demonstrating early stage NSCLC and a plurality of radiological images of the region of tissue.

Apparatus 1100 also includes an input/output (I/O) interface 1130, a set of circuits 1150, and an interface 1140 that connects the processor 1110, the memory 1120, the I/O interface 1130, and the set of circuits 1150. I/O interface 1130 may be configured to transfer data between memory 1120, processor 1110, circuits 1150, and external devices, for example, a CADx system or a personalized medicine system.

The set of circuits 1150 includes a radiomic feature extraction circuit 1151, a pathomic feature extraction circuit 1153, a combined radiomic-pathomic classification circuit 1155, and a display circuit 1157.

Radiomic feature acquisition circuit 1151 is configured to access a radiological image of a region of tissue demonstrating early stage NCSLS. The region of tissue represented in the radiological image includes a tumor region. Radiomic feature acquisition circuit 1151 is further configured to extract a set of radiomic features from the radiological image. In one embodiment, radiomic feature acquisition circuit 1151 is configured to extract the set of radiomic features from the radiological image by segmenting a nodule represented in the radiological image. The nodule has a volume. The radiological image is a three-dimensional (3D) computed tomography (CT) image. In another embodiment, other types of radiological image, including MRI images, may be accessed.

In one embodiment, radiomic feature acquisition circuit 1151 is configured to detect a nodule represented in the radiological image. In one embodiment, radiomic feature acquisition circuit 1151 is configured to use a watershed segmentation technique. In another embodiment, other segmentation techniques, including thresholding, edge-based techniques, or region growing, may be employed.

Radiomic feature acquisition circuit 1151 is further configured to divide the volume into a plurality of slices. A slice has a boundary. The slice has an area defined by the boundary. A slice may be a 2D slice. The number of slices may be a function of the volume of the tumor, may be based on a desired level of computational resource usage, or may be manually selected.

Radiomic feature acquisition circuit 1151 is further configured to select a member of the plurality of slices having the largest area. In one embodiment, if more than one member of the plurality of slices having the largest area have the same area, radiomic feature acquisition circuit 1151 is configured to randomly select a member of the more than one member of the plurality of slices having the largest area.

Radiomic feature acquisition circuit 1151 is further configured to define a peritumoral region based on a morphological dilation of the boundary of the member of the plurality of slices. In another embodiment, radiomic feature acquisition circuit 1151 is configured to define the peritumoral region using other, different morphological operations.

Radiomic feature acquisition circuit 1151 is further configured to extract a set of tumoral features from the member of the plurality of slices. In one embodiment, the set of tumoral features includes at least one of a Gabor feature, a Haralick feature, a Laws feature, a Law-Laplacian feature, or a co-occurrence of local anisotropic gradient orientation (CoLlAGe) feature.

Radiomic feature acquisition circuit 1151 is further configured to extract a set of peritumoral features from the peritumoral region. In one embodiment, the set of peritumoral features includes at least one of a Gabor feature, a Haralick feature, a Laws feature, a Law-Laplacian feature, or a co-occurrence of local anisotropic gradient orientation (CoLlAGe) feature.

Pathomic feature acquisition circuit 1153 is configured to access a digitized pathology image of a region of tissue demonstrating early stage NCSLS. Accessing the digitized pathology image may include accessing the digitized pathology image stored in memory 1120. In one embodiment, accessing the digitized pathology image may including accessing a digitized pathology image stored in a data storage device, including a hard disk drive, a solid state device, a tape drive, accessing a digitized pathology image over a local area network, or from the cloud. Accessing the diagnostic image includes acquiring electronic data, reading from a computer file, receiving a computer file, reading from a computer memory, or other computerized activity. Pathomic feature acquisition circuit 1153 is further configured extract a set of pathomic features from the digitized pathology image. The set of pathomic features includes at least one of a global graph feature, a local nuclear cluster graph feature, a nuclear shape feature, or a nuclear orientation entropy feature.

In one embodiment, pathomic feature acquisition circuit 1153 is configured to detect a member of the plurality of cellular nuclei represented in the digitized pathology image. In one embodiment, pathomic feature acquisition circuit 1153 is configured to detect the member of the plurality of cellular nuclei represented in the diagnostic image using a watershed segmentation technique. In another embodiment, pathomic feature acquisition circuit 1153 may be configured to employ other automated segmentation techniques, including thresholding, edge-based techniques, or region growing.

In one embodiment, pathomic feature extraction circuit 1153 is configured to extract the set of pathomic features by defining a plurality of patches in the digitized pathology image. The digitized pathology image may be a digitized whole slide image (WSI) of a hematoxylin and eosin (H&E) stained tissue slide scanned at 20× magnification.

In this embodiment pathomic feature extraction circuit 1153 is also configured to randomly select a subset of the plurality of patches. The number of elements in the subset is smaller than the number of elements in the plurality.

In this embodiment pathomic feature extraction circuit 1153 is also configured to segment at least two members of a plurality of cellular nuclei represented in at least one member of the subset of the plurality of patches.

In this embodiment pathomic feature extraction circuit 1153 is also configured to extract the set of pathomic features based on the at least two segmented members of plurality of cellular nuclei, where the set of pathomic features includes at least one of a global graph feature, a local nuclear cluster graph feature, a nuclear shape feature, or a nuclear orientation entropy feature.

Combined radiomic-pathomic classification circuit 1155 is configured to compute a probability that the region of tissue will experience NSCLC recurrence. Combined radiomic-pathomic classification circuit 1155 computes the probability based, at least in part, on at least one member of the set of pathomic features and at least one member of the set of radiomic features. Combined radiomic-pathomic classification circuit 1155 is further configured to generate a classification of the region of tissue as likely to experience recurrence or unlikely to experience recurrence based, at least in part, on the probability. In another embodiment, other classification schemes may be employed, including classifying the region of tissue as, for example: recurrent, unknown, or non-recurrent.

In one embodiment combined radiomic-pathomic classification circuit 1155 is configured to compute the probability using a LDA classification approach based on the at least one member of the set of pathomic features and at least one member of the set of radiomic features. In another embodiment, combined radiomic-pathomic classification circuit 1155 is configured as an LDA classifier. In this embodiment, the machine learning classifier is trained on a set of training images. In another embodiment, combined radiomic-pathomic classification circuit 1155 may be configured as another type of machine learning or deep learning classifier, including as a QDA classifier, an RF classifier, or a CNN classifier. In another embodiment, combined radiomic-pathomic classification circuit 1155 is configured to use other machine learning techniques, include deep learning techniques, to compute the probability.

Display circuit 1157 is configured to display the classification. Display circuit 1157 is also configured to display at least one of the probability, the at least one member of the set of radiomic features, the at least one member of the set of pathomic features, the set of radiomic features, the set of pathomic features, the radiological image, or the digitized pathology image. Displaying at least one of the probability, the at least one member of the set of radiomic features, the at least one member of the set of pathomic features, the set of radiomic features, the set of pathomic features, the radiological image, or the digitized pathology image may also include printing the at least one of the probability, the at least one member of the set of radiomic features, the at least one member of the set of pathomic features, the set of radiomic features, the set of pathomic features, the radiological image, or the digitized pathology image. Display circuit 1157 may also control a CADx system, a monitor, or other display, to display operating parameters or characteristics of radiomic feature extraction circuit 1151, pathomic feature extraction circuit 1153, combined radiomic-pathomic classification circuit 1155, including a machine learning classifier, during both training and testing, or during clinical operation of apparatus 1100 or apparatus 1200.

Figure 12:
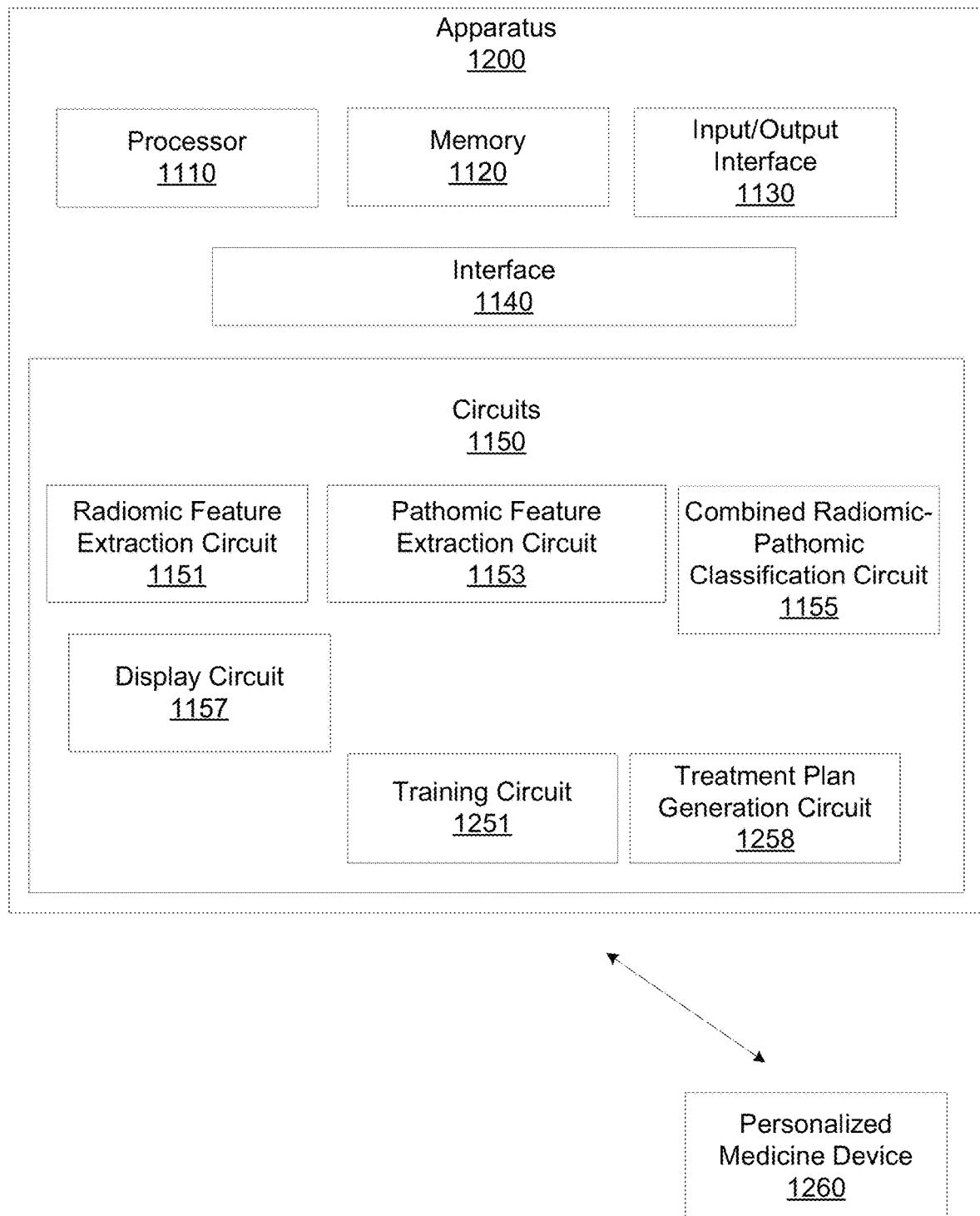
FIG. 12 illustrates an example apparatus for predicting recurrence of early stage NSCLC.

FIG. 12 illustrates an apparatus 1200 that is similar to apparatus 1100 but that includes additional elements and details. Apparatus 1200 includes a treatment plan generation circuit 1258. Treatment plan generation circuit 1258 is configured to generate a personalized treatment plan based, at least in part, on the classification. In one embodiment, the personalized treatment plan is further based on the digitized pathology image, the radiological image, the set of pathomic features, or the set of radiomic features. The personalized treatment plan may suggest a surgical treatment, may define an immunotherapy agent dosage or schedule, or a chemotherapy agent dosage or schedule, when the region of tissue is classified as likely to experience recurrence. For a region of tissue classified as unlikely to experience recurrence, other treatments, schedules, or dosages may be suggested.

In one embodiment, apparatus 1200 also includes training circuit 1251. Training circuit 1251 is configured to train combined radiomic-pathomic classification circuit 1155 according to techniques described herein. Training combined radiomic-pathomic classification circuit 1155 may include training a machine learning classifier, including a LDA classifier. In one embodiment, training circuit 1251 is configured to access a training dataset of digitized images of a region of interest demonstrating early stage NSCLC. The training dataset includes digitized pathology images and radiological images of tissue that experience recurrence, and digitized pathology images and radiological images of tissue that did not experience recurrence. Training circuit 1251 may be further configured to access a testing dataset of digitized pathology images and radiological images of a region of interest demonstrating early stage NSCLC, where the testing dataset includes digitized pathology images and radiological images of tissue that experience recurrence, and digitized pathology images and radiological images of tissue that did not experience recurrence. In this embodiment, the machine learning classifier is trained and tested using the training dataset of images and the testing dataset of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 12 further illustrates a personalized medicine device 1260. Apparatus 1200 may be configured to transmit at least one of the classification, the probability, the at least one member of the set of radiomic features, the at least one member of the set of pathomic features, the set of radiomic features, the set of pathomic features, the radiological image, or the digitized pathology image to the personalized medicine device 1260. Personalized medicine device 1260 may be, for example, a CADx system, an early stage NSCLC recurrence prediction system, or other type of personalized medicine device that may be used to facilitate the classification of tissue. In one embodiment, treatment plan generation circuit 1258 may control personalized medicine device 1260 to display the classification, the probability, the at least one member of the set of radiomic features, the at least one member of the set of pathomic features, the set of radiomic features, the set of pathomic features, the radiological image, or the digitized pathology image on a computer monitor, a smartphone display, a tablet display, or other displays.

Figure 13:
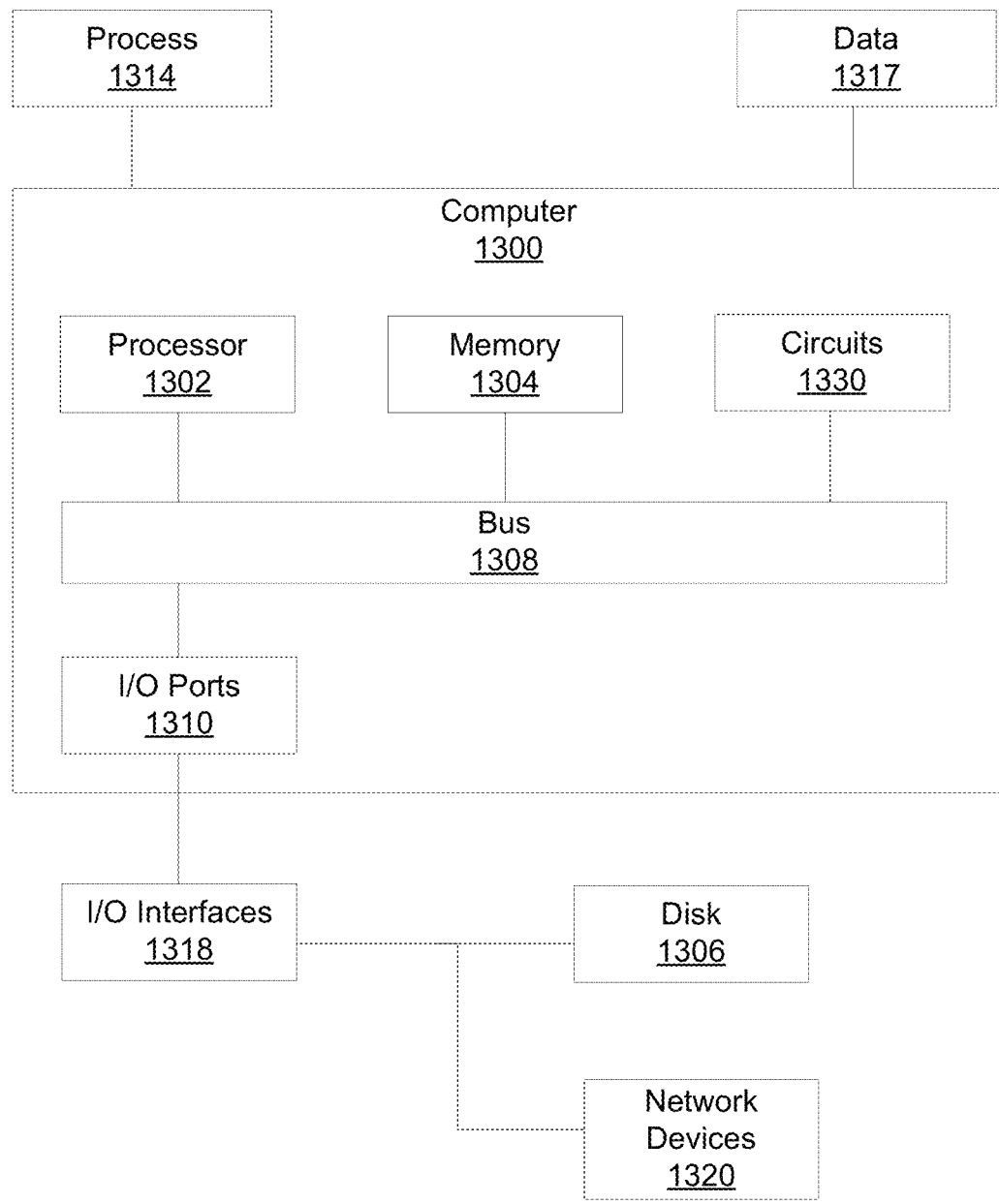
FIG. 13 illustrates an example computer in which embodiments described herein may operate.

FIG. 13 illustrates an example computer 1300 in which example methods illustrated herein can operate and in which example methods, apparatus, circuits, operations, or logics may be implemented. In different examples, computer 1300 may be part of a personalized medicine system, an early stage NSCLC recurrence prediction system, an MRI system, a digital whole slide scanner, a CT system, may be operably connectable to an early stage NSCLC recurrence prediction system, a CT system, an MRI system, a personalized medicine system, or a digital whole slide scanner, or may be part of a CADx system.

Computer 1300 includes a processor 1302, a memory 1304, and input/output (I/O) ports 1310 operably connected by a bus 1308. In one example, computer 1300 may include a set of logics or circuits 1330 that perform a method of predicting early stage NSCLC recurrence in digitized H&E stained images using a machine learning classifier. Thus, the set of circuits 1330, whether implemented in computer 1300 as hardware, firmware, software, and/or a combination thereof may provide means (e.g., hardware, firmware, circuits) for predicting NSCLC recurrence, or characterizing a region of tissue as likely or unlikely to experience NSCLC recurrence. In different examples, the set of circuits 1330 may be permanently and/or removably attached to computer 1300.

Processor 1302 can be a variety of various processors including dual microprocessor and other multi-processor architectures. Processor 1302 may be configured to perform steps of methods claimed and described herein. Memory 1304 can include volatile memory and/or non-volatile memory. A disk 1306 may be operably connected to computer 1300 via, for example, an input/output interface (e.g., card, device) 1318 and an input/output port 1310. Disk 1306 may include, but is not limited to, devices like a magnetic disk drive, a tape drive, a Zip drive, a flash memory card, or a memory stick. Furthermore, disk 1306 may include optical drives like a CD-ROM or a digital video ROM drive (DVD ROM). Memory 1304 can store processes 1314 or data 1317, for example. Data 1317 may, in one embodiment, include digitized images of a region of lung tissue demonstrating early stage NSCLC. Disk 1306 or memory 1304 can store an operating system that controls and allocates resources of computer 1300.

Bus 1308 can be a single internal bus interconnect architecture or other bus or mesh architectures. While a single bus is illustrated, it is to be appreciated that computer 1300 may communicate with various devices, circuits, logics, and peripherals using other buses that are not illustrated (e.g., PCIE, SATA, Infiniband, 794, USB, Ethernet).

Computer 1300 may interact with input/output devices via I/O interfaces 1318 and input/output ports 1310. Input/output devices can include, but are not limited to, CT systems, MRI systems, digital whole slide scanners, an optical microscope, a keyboard, a microphone, a pointing and selection device, cameras, video cards, displays, disk 1306, network devices 1320, or other devices. Input/output ports 1310 can include but are not limited to, serial ports, parallel ports, or USB ports.

Computer 1300 may operate in a network environment and thus may be connected to network devices 1320 via I/O interfaces 1318 or I/O ports 1310. Through the network devices 1320, computer 1300 may interact with a network. Through the network, computer 1300 may be logically connected to remote computers. The networks with which computer 1300 may interact include, but are not limited to, a local area network (LAN), a wide area network (WAN), or other networks, including the cloud.

Figure 14:
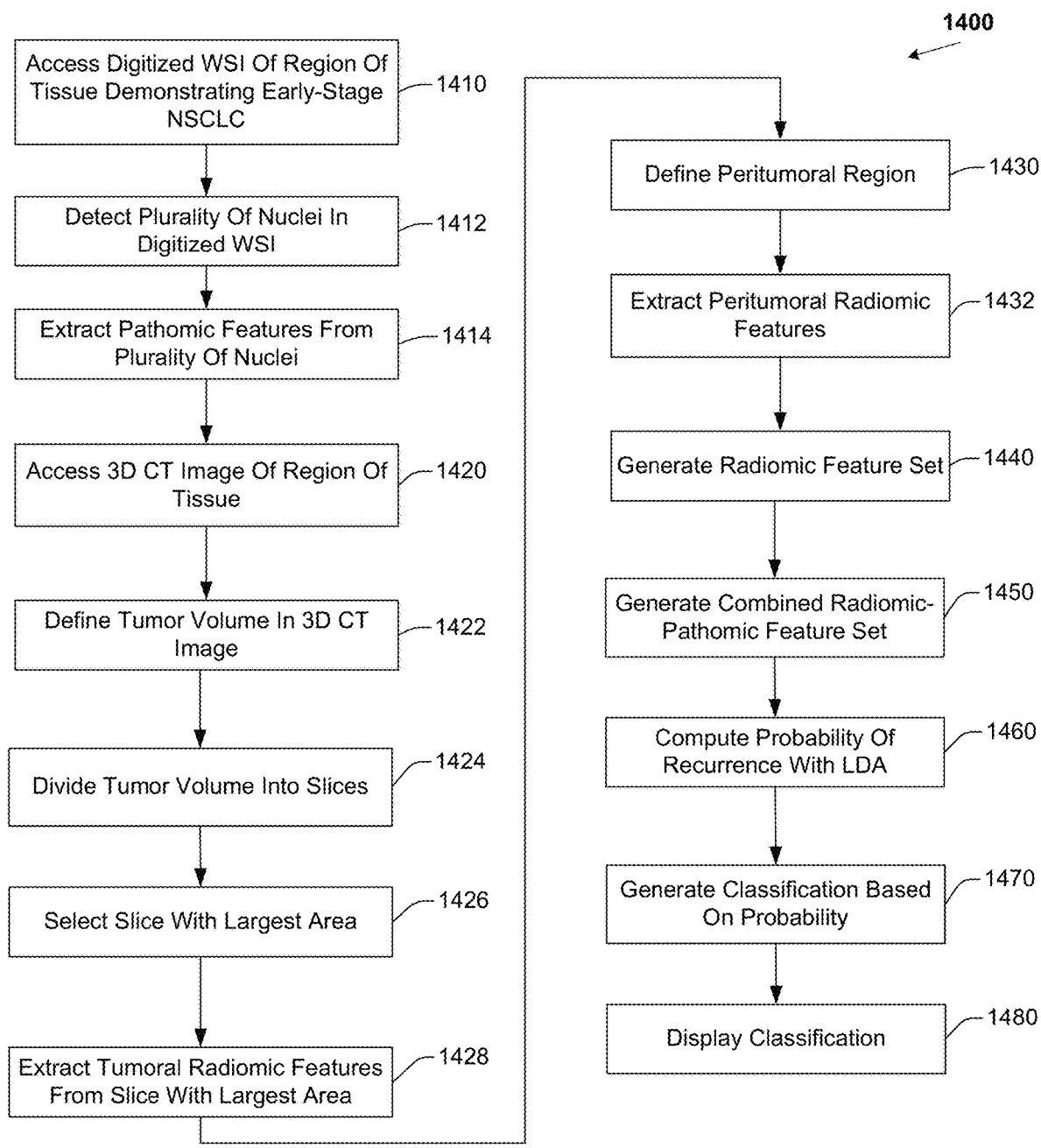
FIG. 14 illustrates an example method for predicting recurrence of early stage NSCLC.

FIG. 14 illustrates an example method 1400 for predicting early stage NSCLC recurrence using a combined radiomic-pathomic feature set extracted from a radiological image and a digitized pathology image at different scales, respectively. Method 1400 includes, at 1410 accessing a digitized WSI of a region of tissue demonstrating early stage NSCLC, the digitized WSI having a plurality of pixels. A pixel has an intensity. The region of tissue includes a tumor region. Accessing the digitized WSI includes acquiring electronic data, reading from a computer file, receiving a computer file, reading from a computer memory, or other computerized activity.

Method 1400 also includes, at 1412, identifying a plurality of cellular nuclei represented in the tumor region. Identifying the plurality of cellular nuclei may include using automated segmentation techniques, including watershed segmentation, or other techniques, including deep learning segmentation techniques.

Method 1400 also includes, at 1414, extracting a set of pathomic features from the plurality of cellular nuclei. The set of pathomic features includes at least one of a global graph feature, a local nuclear cluster graph feature, a nuclear shape feature, or a nuclear orientation entropy feature.

Method 1400 also includes, at 1420, accessing a 3D CT image of the region of tissue. The 3D CT image has a plurality of pixels, a pixel having an intensity. Accessing the 3D CT image includes acquiring electronic data, reading from a computer file, receiving a computer file, reading from a computer memory, or other computerized activity Method 1400 also includes, at 1422, defining a tumor volume by segmenting the tumor region represented in the 3D CT image. In one embodiment, the tumor region may be segmented using a watershed segmentation technique, a region growing technique, thresholding, or deep learning techniques. In another embodiment, the tumor region may be segmented manually.

Method 1400 also includes, at 1424, dividing the tumor volume into a plurality of slices. A slice may be a 2D slice. A slice has a boundary. The slice has an area defined by the boundary.

Method 1400 also includes, at 1426, selecting a member of the plurality of slices having the largest area. In one embodiment, selecting a member of the plurality of slices having the largest area may include randomly selecting, from among members of the plurality of slices having the same area, a member of the plurality of slices.

Method 1400 also includes, at 1428, extracting a set of tumoral features from the member of the plurality of slices. The set of tumoral features includes at least one of a Gabor feature, a Haralick feature, a Laws feature, a Law-Laplacian feature, or a CoLIAGe feature.

Method 1400 also includes, at 1430, defining a peritumoral region based on a morphological dilation of the boundary of the member of the plurality of slices. In one embodiment, the peritumoral region includes five annular rings, an annular ring having a dilation value of 2 mm.

Method 1400 also includes, at 1432, extracting a set of peritumoral features from the peritumoral region. The set of peritumoral features includes at least one of a Gabor feature, a Haralick feature, a Laws feature, a Law-Laplacian feature, or a CoLIAGe feature.

Method 1400 also includes, at 1440, generating a radiomic feature set from the set of tumoral features and the set of peritumoral features. The radiomic feature set includes at least one feature selected from the set of tumoral features or at least one feature selected from the set of peritumoral features.

Method 1400 also includes, at 1450, generating a combined radiomic-pathomic feature set. The combined radiomic-pathomic feature set includes at least one feature selected from the set of pathomic features, and at least one feature selected from the radiomic feature set.

Method 1400 also includes, at 1460, computing, using an LDA machine learning classifier, a probability that the region of tissue will experience NSCLC recurrence based, at least in part, on the combined feature set. In another embodiment, other machine learning techniques, including QDA, random forests, or convolutional neural networks may be employed.

Method 1400 also includes, at 1470, generating a classification of the region of tissue as recurrent or non-recurrent based, at least in part, on the probability. In another embodiment, other classification schemes may be employed. For example, the region of tissue may be classified as recurrent, unknown, or non-recurrent, based on the probability.

Method 1400 further includes, at 1480, displaying the classification and at least one of the pathology image, the radiological image, the set of pathomic features, the set of radiomic features, the combined feature set, or the probability. Displaying the classification and at least one of the pathology image, the radiological image, the set of pathomic features, the set of radiomic features, the combined feature set, or the probability includes acquiring electronic data, reading from a computer file, receiving a computer file, reading from a computer memory, or other computerized activity.

Figure 15:
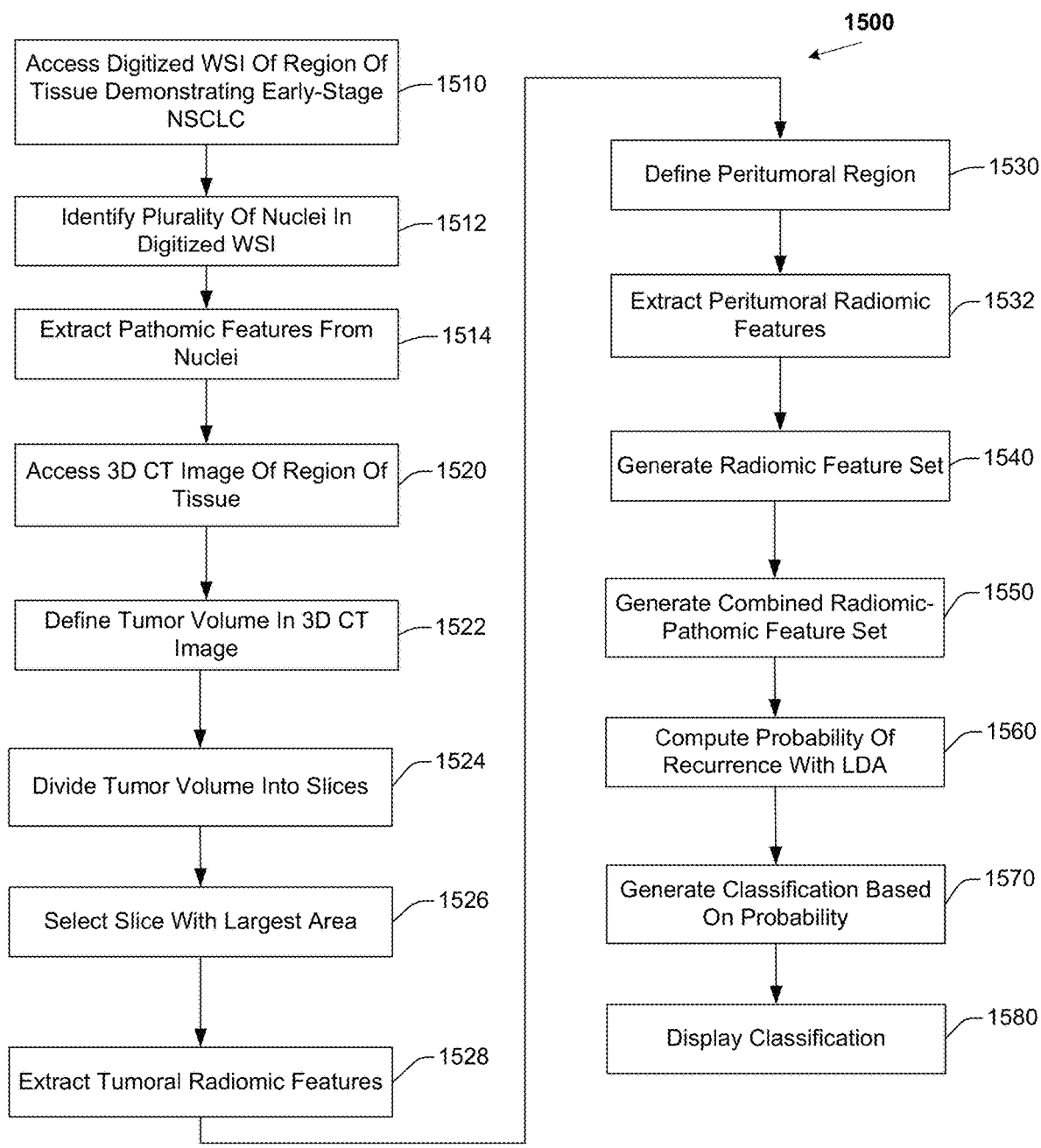
FIG. 15 is a flow diagram of example operations for predicting recurrence of early stage NSCLC.

FIG. 15 is a flow diagram of example operations 1500 that may be performed by a processor for predicting early stage NSCLC recurrence. The set of operations 1500 includes, at 1510 accessing a digitized WSI of a region of tissue demonstrating early stage NSCLC. The digitized WSI has a plurality of pixels, a pixel having an intensity. The region of tissue includes a tumor region.

The set of operations 1500 also includes, at 1512, identifying a plurality of cellular nuclei represented in the tumor region. The plurality of cellular nuclei may be identified using automated, machine learning-based segmentation techniques.

The set of operations 1500 also includes, at 1514, extracting a set of pathomic features from the plurality of cellular nuclei at a first scale. The set of pathomic features includes at least one of a global graph feature, a local nuclear cluster graph feature, a nuclear shape feature, or a nuclear orientation entropy feature.

The set of operations 1500 also includes, at 1520, accessing a 3D CT image of the region of tissue. The 3D CT image has a plurality of pixels, a pixel having an intensity.

The set of operations 1500 also includes, at 1522, defining a tumor volume by segmenting the tumor region represented in the 3D CT image. The tumor region may be segmented using, for example, watershed segmentation, region growing, thresholding, or other segmentation techniques.

The set of operations 1500 also includes, at 1524, dividing the tumor volume into a plurality of slices. A slice has a boundary. A slice has an area defined by the boundary.

The set of operations 1500 also includes, at 1526, selecting a member of the plurality of slices having the largest area.

The set of operations 1500 also includes, at 1528, extracting a set of tumoral features from the member of the plurality of slices having the largest area, at a second different scale. The set of tumoral features includes at least one of a Gabor feature, a Haralick feature, a Laws feature, a Law-Laplacian feature, or a CoLlAGe feature.

The set of operations 1500 also includes, at 1530, defining a peritumoral region based on a morphological dilation of the boundary of the member of the plurality of slices. In one embodiment, the peritumoral region includes five annular rings, dilated at 2 mm increments from the boundary.

The set of operations 1500 also includes, at 1532, extracting a set of peritumoral features from the peritumoral region at the second, different scale. The set of peritumoral features includes at least one of a Gabor feature, a Haralick feature, a Laws feature, a Law-Laplacian feature, or a CoLlAGe feature.

The set of operations 1500 also includes, at 1540, generating a radiomic feature set from the set of tumoral features and the set of peritumoral features. The radiomic feature set includes at least one feature selected from the set of tumoral features or at least one feature selected from the set of peritumoral features.

The set of operations 1500 also includes, at 1550, generating a combined radiomic-pathomic feature set. The combined radiomic-pathomic feature set includes at least one feature selected from the set of pathomic features, and at least one feature selected from the radiomic feature set. In one embodiment, the combined radiomic-pathomic feature set includes two peritumoral radiomic Haralick features and two pathomic shape features.

The set of operations 1500 also includes, at 1560, computing, using an LDA machine learning classifier, a probability that the region of tissue will experience NSCLC recurrence. The LDA machine learning classifier computes the probability based, at least in part, on the combined feature set.

The set of operations 1500 also includes, at 1570, generating a classification of the region of tissue as recurrent or non-recurrent. The classification is based, at least in part, on the probability.

The set of operations 1500 also includes, at 1580, displaying the classification and at least one of the pathology image, the radiological image, the set of pathomic features, the set of radiomic features, the combined feature set, or the probability. The classification and at least one of the pathology image, the radiological image, the set of pathomic features, the set of radiomic features, the combined feature set, or the probability may be displayed on a computer monitor, a smartphone display, a tablet display, or other electronic display device.

Examples herein can include subject matter such as an apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for classifying a region of tissue demonstrating NSCLC, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a non-small cell lung cancer (NSCLC) recurrence prediction system to perform operations, the operations comprising:
    accessing a pathology image of a region of tissue demonstrating early stage non-small cell lung cancer (NSCLC);
    extracting a set of pathomic features from the pathology image;
    accessing a radiological image of the region of tissue;
    extracting a set of radiomic features from the radiological image;
    generating a combined feature set, where the combined feature set includes at least one member of the set of pathomic features, and at least one member of the set of radiomic features;
    computing a probability that the region of tissue will experience NSCLC recurrence based, at least in part, on the combined feature set; and
    classifying the region of tissue as recurrent or non-recurrent based, at least in part, on the probability.

2. The non-transitory computer-readable storage device of claim 1, where the pathology image includes a plurality of cellular nuclei.

3. The non-transitory computer-readable storage device of claim 2, where extracting the set of pathomic features includes:
    segmenting at least two members of the plurality of cellular nuclei represented in the pathology image; and
    extracting the set of pathomic features based on the at least two segmented members of plurality of cellular nuclei.

4. The non-transitory computer-readable storage device of claim 3, where segmenting at least two members of the plurality of cellular nuclei includes segmenting the at least two members of the plurality of cellular nuclei using a convolutional neural network (CNN).

5. The non-transitory computer-readable storage device of claim 3, where the set of pathomic features includes at least one of a global graph feature, a local nuclear cluster graph feature, a nuclear shape feature, or a nuclear orientation entropy feature.

6. The non-transitory computer-readable storage device of claim 1, where the pathology image is a digitized whole slide image (WSI) of a hematoxylin and eosin (H&E) stained tissue slide scanned at 20× magnification.

7. The non-transitory computer-readable storage device of claim 6, where the set of pathomic features are extracted from a plurality of patches selected randomly from the pathology image, where a patch has dimensions of 1000 pixels by 1000 pixels.

8. The non-transitory computer-readable storage device of claim 1, where the radiological image is a three dimensional (3D) computed tomography (CT) image.

9. The non-transitory computer-readable storage device of claim 8, where extracting the set of radiomic features from the radiological image includes:
    segmenting a tumor represented in the radiological image, where the tumor has a volume;
    dividing the volume into a plurality of slices, where a slice has a boundary, where a slice has an area defined by the boundary;
    selecting a member of the plurality of slices having the largest area;
    extracting a set of tumoral features from the member of the plurality of slices;
    defining a peritumoral region based on the boundary of the member of the plurality of slices; and
    extracting a set of peritumoral features from the peritumoral region.

10. The non-transitory computer-readable storage device of claim 9, where the peritumoral region includes five annular rings;
    where an annular ring is defined using morphological dilation of the boundary of the member of the plurality of slices using a dilation increment of 2 mm per annular ring.

11. The non-transitory computer-readable storage device of claim 9, where the set of radiomic features includes at least one of a Gabor feature, a Haralick feature, a Laws feature, a Law-Laplacian feature, or a co-occurrence of local anisotropic gradient orientation (CoLIAGe) feature.

12. The non-transitory computer-readable storage device of claim 9, where the set of radiomic features is extracted from a 5 mm by 5 mm window of the radiological image.

13. The non-transitory computer-readable storage device of claim 1, where computing the probability that the region of tissue will experience recurrence includes:
    providing the combined feature set to a machine learning classifier; and receiving, from the machine learning classifier, the probability, where the machine learning classifier computes the probability based, at least in part, on the combined feature set.

14. The non-transitory computer-readable storage device of claim 13, where the machine learning classifier is a linear discriminant analysis (LDA) classifier configured to discriminate early stage NSCLC tissue that experiences recurrence from early stage NSCLC tissue that does not experience recurrence.

15. The non-transitory computer-readable storage device of claim 1, the operations further comprising:
displaying the classification and at least one of the pathology image, the radiological image, the set of pathomic features, the set of radiomic features, the combined feature set, or the probability.

16. The non-transitory computer-readable storage device of claim 1, where the set of pathomic features are extracted from the pathology image at a first scale, and where the set of radiomic features are extracted from the radiological image at a second, different scale.

17. An apparatus for predicting recurrence in early stage non-small cell lung cancer (NSCLC), comprising:
a processor;
a memory configured to store a digitized pathology image of a tissue slide of a region of tissue demonstrating early stage NSCLC, and a radiological image of the region of tissue;
an input/output (I/O) interface;
a set of circuits; and
an interface that connects the processor, the memory, the I/O interface, and the set of circuits, the set of circuits comprising:
a radiomic feature extraction circuit configured to:
access the radiological image; and
extract a set of radiomic features from the radiological image;
a pathomic feature extraction circuit configured to:
access the digitized pathology image; and
extract a set of pathomic features from the digitized pathology image;
a combined radiomic-pathomic classification circuit configured to:
compute a probability that the region of tissue will experience NSCLC recurrence based on at least one member of the set of pathomic features and at least one member of the set of radiomic features; and
generate a classification of the region of tissue as likely to experience recurrence or unlikely to experience recurrence based, at least in part, on the probability; and
a display circuit configured to display the classification and at least one of the probability, the at least one member of the set of radiomic features, the at least one member of the set of pathomic features, the set of radiomic features, the set of pathomic features, the radiological image, or the digitized pathology image.

18. The apparatus of claim 17, where the radiomic feature extraction circuit is further configured to extract the set of radiomic features from the radiological image by:
segmenting a nodule represented in the radiological image, where the nodule has a volume, where the radiological image is a three-dimensional (3D) computed tomography (CT) image;
dividing the volume into a plurality of slices, where a slice has a boundary, where the slice has an area defined by the boundary;
selecting a member of the plurality of slices having the largest area;
defining a peritumoral region based on a morphological dilation of the boundary of the member of the plurality of slices;
extracting a set of tumoral features from the member of the plurality of slices; and
extracting a set of peritumoral features from the peritumoral region;
where the set of radiomic features includes at least one of a Gabor feature, a Haralick feature, a Laws feature, a Law-Laplacian feature, or a co-occurrence of local anisotropic gradient orientation (CoLIAGe) feature selected from the set of tumoral features or the set of peritumoral features.

19. The apparatus of claim 17, where the pathomic feature extraction circuit is further configured to extract the set of pathomic features by:
defining a plurality of patches in the digitized pathology image, where the digitized pathology image is a digitized whole slide image (WSI) of a hematoxylin and eosin (H&E) stained tissue slide scanned at 20× magnification;
randomly selecting a subset of the plurality of patches, where the number of elements in the subset is smaller than the number of elements in the plurality;
segmenting at least two members of a plurality of cellular nuclei represented in at least one member of the subset; and
extracting the set of pathomic features based on the at least two segmented members of plurality of cellular nuclei;
where the set of pathomic features includes at least one of a global graph feature, a local nuclear cluster graph feature, a nuclear shape feature, or a nuclear orientation entropy feature.

20. The apparatus of claim 17, where the combined radiomic-pathomic classification circuit is configured to compute the probability using a linear discriminant analysis (LDA) classification approach.

21. A non-transitory computer-readable storage device storing computer-executable instructions that when executed control a computer to perform a method, the method comprising:
accessing a digitized whole slide image (WSI) of a region of tissue demonstrating early stage non-small cell lung cancer (NSCLC), the digitized WSI having a plurality of pixels, a pixel having an intensity, where the region of tissue includes a tumor region;
identifying a plurality of cellular nuclei represented in the tumor region;
extracting a set of pathomic features from the plurality of cellular nuclei, where the set of pathomic features includes at least one of a global graph feature, a local nuclear cluster graph feature, a nuclear shape feature, or a nuclear orientation entropy feature;
accessing a three dimensional (3D) computed tomography (CT) image of the region of tissue, the 3D CT image having a plurality of pixels, a pixel having an intensity;
defining a tumor volume by segmenting the tumor region represented in the 3D CT image;
dividing the tumor volume into a plurality of slices, where a slice has a boundary, where the slice has an area defined by the boundary;
selecting a member of the plurality of slices having the largest area;

extracting a set of tumoral features from the member of the plurality of slices, where the set of tumoral features includes at least one of a Gabor feature, a Haralick feature, a Laws feature, a Law-Laplacian feature, or a co-occurrence of local anisotropic gradient orientation (CoLIAGe) feature;

defining a peritumoral region based on a morphological dilation of the boundary of the member of the plurality of slices;

extracting a set of peritumoral features from the peritumoral region, where the set of peritumoral features includes at least one of a Gabor feature, a Haralick feature, a Laws feature, a Law-Laplacian feature, or a co-occurrence of local anisotropic gradient orientation (CoLIAGe) feature;

generating a radiomic feature set from the set of tumoral features and the set of peritumoral features, where the radiomic feature set includes at least one feature selected from the set of tumoral features or at least one feature selected from the set of peritumoral features;

generating a combined radiomic-pathomic feature set, where the combined radiomic-pathomic feature set includes at least one feature selected from the set of pathomic features, and at least one feature selected from the radiomic feature set;

computing, using a linear discriminant analysis (LDA) machine learning classifier, a probability that the region of tissue will experience NSCLC recurrence based, at least in part, on the combined feature set;

generating a classification of the region of tissue as recurrent or non-recurrent based, at least in part, on the probability; and displaying the classification and at least one of the pathology image, the radiological image, the set of pathomic features, the set of radiomic features, the combined feature set, or the probability.

22. A non-transitory computer readable storage device storing computer-executable instructions that when executed control a processor to perform operations, the operations comprising:

accessing a digitized whole slide image (WSI) of a region of tissue demonstrating early stage non-small cell lung cancer (NSCLC), the digitized WSI having a plurality of pixels, a pixel having an intensity, where the region of tissue includes a tumor region;

identifying a plurality of cellular nuclei represented in the tumor region;

extracting a set of pathomic features from the plurality of cellular nuclei at a first scale, where the set of pathomic features includes at least one of a global graph feature, a local nuclear cluster graph feature, a nuclear shape feature, or a nuclear orientation entropy feature;

accessing a three dimensional (3D) computed tomography (CT) image of the region of tissue, the 3D CT image having a plurality of pixels, a pixel having an intensity;

defining a tumor volume by segmenting the tumor region represented in the 3D CT image;

dividing the tumor volume into a plurality of slices, where a slice has a boundary, where the slice has an area defined by the boundary;

selecting a member of the plurality of slices having the largest area;

extracting a set of tumoral features from the member of the plurality of slices at a second different scale, where the set of tumoral features includes at least one of a Gabor feature, a Haralick feature, a Laws feature, a Law-Laplacian feature, or a co-occurrence of local anisotropic gradient orientation (CoLIAGe) feature;

defining a peritumoral region based on a morphological dilation of the boundary of the member of the plurality of slices;

extracting a set of peritumoral features from the peritumoral region at the second, different scale, where the set of peritumoral features includes at least one of a Gabor feature, a Haralick feature, a Laws feature, a Law-Laplacian feature, or a co-occurrence of local anisotropic gradient orientation (CoLIAGe) feature;

generating a radiomic feature set from the set of tumoral features and the set of peritumoral features, where the radiomic feature set includes at least one feature selected from the set of tumoral features or at least one feature selected from the set of peritumoral features;

generating a combined radiomic-pathomic feature set, where the combined radiomic-pathomic feature set includes at least one feature selected from the set of pathomic features, and at least one feature selected from the radiomic feature set;

computing, using a linear discriminant analysis (LDA) machine learning classifier, a probability that the region of tissue will experience NSCLC recurrence based, at least in part, on the combined feature set;

generating a classification of the region of tissue as recurrent or non-recurrent based, at least in part, on the probability; and displaying the classification and at least one of the pathology image, the radiological image, the set of pathomic features, the set of radiomic features, the combined feature set, or the probability.

* * * * *